(12) United States Patent
Nakajima et al.

(10) Patent No.: US 8,029,486 B2
(45) Date of Patent: Oct. 4, 2011

(54) DISPOSABLE WEARING ARTICLE

(75) Inventors: Kaiyo Nakajima, Kagawa-ken (JP); Yoshitaka Mishima, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 124 days.

(21) Appl. No.: 12/469,816

(22) Filed: May 21, 2009

(65) Prior Publication Data
US 2009/0234316 A1    Sep. 17, 2009

Related U.S. Application Data

(62) Division of application No. 11/038,486, filed on Jan. 21, 2005, now Pat. No. 7,563,257.

(30) Foreign Application Priority Data

Jul. 9, 2004  (JP) .................................. 2004-203171

(51) Int. Cl.
*A61F 13/15*    (2006.01)
(52) U.S. Cl. ........... 604/385.19; 604/385.3; 604/385.12; 604/385.04
(58) Field of Classification Search ............. 604/385.19, 604/385.3, 385.12, 385.04
See application file for complete search history.

(56) References Cited

U.S. PATENT DOCUMENTS

| | | | |
|---|---|---|---|
| 5,558,661 A | 9/1996 | Roe et al. | |
| 5,667,503 A | 9/1997 | Roe et al. | |
| 6,165,160 A | 12/2000 | Suzuki et al. | |
| 6,248,098 B1 | 6/2001 | Sayama | |
| 6,383,170 B1 | 5/2002 | Mishima et al. | |
| 6,406,465 B1 | 6/2002 | Otsubo | |
| 6,471,682 B2 | 10/2002 | Kashiwagi | ............... 604/385.27 |
| 6,638,260 B2 | 10/2003 | Mishima | |
| 6,699,228 B1 | 3/2004 | Chimielewski et al. | |
| 2001/0016719 A1 | 8/2001 | Mishima | |
| 2002/0077615 A1 | 6/2002 | Mishima | |
| 2002/0151861 A1 | 10/2002 | Klemp et al. | ............ 604/385.19 |

FOREIGN PATENT DOCUMENTS

| | | |
|---|---|---|
| EP | 0955028 | 11/1999 |
| EP | 1 064 899 A1 | 1/2001 |
| EP | 1 114 631 A2 | 7/2001 |
| EP | 1 234 563 A3 | 8/2002 |
| EP | 1 323 399 A2 | 7/2003 |
| JP | 1 224 922 A3 | 9/1989 |
| JP | 5-285174 | 11/1993 |
| JP | 8-196565 | 8/1996 |
| JP | 8-322878 | 12/1996 |
| JP | 11-318976 | 11/1999 |
| JP | 11-342156 | 12/1999 |

(Continued)

*Primary Examiner* — Jacqueline F Stephens
(74) *Attorney, Agent, or Firm* — Lowe, Hauptman, Ham & Berner, LLP

(57) ABSTRACT

A disposable wearing article is provided with a skin-contactable panel laid in a front half of a crotch region of the article and a liquid-impervious partition laid in a vicinity of a transverse center line of the article. The panel has transversely opposite side edges bonded to transverse opposite side portion of the article and a intermediate region defined between these side edges. The partition has an upper edge bonded to the panel, a lower edge bonded to a topsheet of the article transversely opposite side edges bonded to the side portions of the article and a middle portion defined between the upper and lower edges. The intermediate region of the panel describes an upward convex circular arc above the topsheet and the middle portion of the partition is unfolded in a thickness direction of the article so as to form a pocket-like barrier against movement of bodily wastes.

11 Claims, 21 Drawing Sheets

FOREIGN PATENT DOCUMENTS

| | | |
|---|---|---|
| JP | 2002-336301 | 11/2002 |
| JP | 2002-369839 | 12/2002 |
| JP | 2003-180735 | 7/2003 |
| JP | 2003-325563 A | 11/2003 |
| JP | 2004-008301 | 1/2004 |
| JP | 2004-73625 | 3/2004 |
| WO | 9963921 A1 | 12/1999 |

DISPOSABLE WEARING ARTICLE

RELATED APPLICATIONS

The present application is a divisional of, and claims priority from, U.S. patent application Ser. No. 11/038,486, filed Jan. 21, 2005 (now U.S. Pat. No. 7,563,257), and Japanese Application Number 2004-203171, filed Jul. 9, 2004, the disclosures of which are hereby incorporated by reference herein in their entirety.

BACKGROUND OF THE INVENTION

The present invention relates to a disposable wearing article adapted for absorption and containment of bodily wastes.

In Japanese Unexamined Patent Application Publication No. 1999-318976 (hereinafter referred to as "Citation"), there has already been proposed a disposable wearing article configured by a front waist region, a rear waist region, a crotch region extending between these two waist regions, longitudinally opposite end portions extending across the respective waist regions in a transverse direction and transversely opposite side edge portions extending between the front and rear waist regions in a longitudinal direction. The wearing article comprises a liquid-pervious topsheet facing the article wearer's skin, a liquid-impervious backsheet facing away the article wearer's skin, a pair of liquid-impervious leak-barrier sheets normally biased to rise above the topsheet under a contractile force of stretchably elastic members extending in the longitudinally direction and attached in stretched state to the respective leak-barrier sheets, a liquid-absorbent core interposed between the top- and backsheets so as to extend between the front and rear waist regions and formed with a plurality of raised ridges, each extending in the transverse direction, spaced apart one from another by a predetermined dimension in the longitudinal direction, and a sheet member attached to the upper surface of the topsheet so that this sheet member may rise up above from the upper surface of the topsheet.

The raised ridges are formed in a rear half of the crotch region divided by a transverse center line bisecting a longitudinal dimension of the article and in the rear waist region. In this known article, it is claimed that loose passage discharged onto the article in the rear half of the crotch region and in the rear waist region is prevented by the raised ridges and the sheet member from flowing forward into a front half of the crotch region and further flowing forward into the front waist region whereby the article wearer's genital organ is protected from being contaminated with loose passage.

However, the article disclosed in Citation creates a problem such that the sheet member may readily collapse as the wearer's body weight is exerted on the crotch region which is thereby compressed into the wearer's crotch region transversely inward. The sheet member having collapsed in this manner can no more function as a barrier adapted to prevent loose passage from further flowing beyond this barrier and consequentially loose passage may flow beyond this sheet member into the front half of the crotch region and even into the front waist region. In the case of this wearing article, the article wearer's genital organ is always in contact with the outer surface of the topsheet during use of the article, so the wearer's genital organ may be contaminated with loose passage spreading over the outer surface of the topsheet if loose passage flows into the front half of the crotch region and further into the front waist region.

SUMMARY OF THE INVENTION

It is an object of the present invention to provide a disposable wearing article improved so that flow of loose passage can be appropriately banked up to protect the wearer's genital organ reliably from being contaminated with loose passage.

According to a first aspect of the present invention, there is provided a disposable wearing article configured by a front waist region, a rear waist region, a crotch region extending between these two waist regions, longitudinally opposite end portions extending across the respective waist regions in a transverse direction and transversely opposite side portions extending between the front and rear waist regions in a longitudinal direction, the article comprising a liquid-pervious topsheet facing the wearer's skin, a liquid-impervious backsheet facing away the wearer's skin and a liquid-absorbent core interposed between the top- and backsheets so as to extend between the front and rear waist regions.

The article according to the present invention in the first aspect further comprises a skin-contactable panel laid on the topsheet in the front waist region and a front half of the crotch region divided by a transverse center line bisecting a longitudinal dimension of the article, at least in the front half of the crotch region, and a partition interposed between the topsheet and the panel extending in the transverse direction in a vicinity of the transverse center line; and the panel having transversely opposite side edges bonded to the opposite side portions of the article and an intermediate region defined between the side edges, and the partition having an upper edge bonded to the panel, a lower edge bonded to the topsheet and a middle portion folded in a thickness direction of the article.

The present invention in the first aspect may include preferred embodiments as follow:

The article further comprises a pair of leak-barrier cuffs extending in the longitudinal direction on the topsheet, these leak-barrier cuffs having proximal portions bonded to the side portions of the article so as to extend in the longitudinal direction, distal portions extending in the longitudinal direction and normally biased to rise up above the topsheet and longitudinally opposite end portions of the respective leak-barrier cuffs collapsed in the transverse direction and bonded to the opposite end portions of the article in such a collapsed state wherein stretchable elastic members extending in the longitudinal direction are contractibly attached to the distal portions of the leak-barrier cuffs; and the panel and the partition being laid between the leak-barrier cuffs wherein the intermediate region of the panel is bonded to the distal portions of the leak-barrier cuffs at least at transversely opposite ends of an inner end of the intermediate region adjacent the transverse center line and the intermediate region of the panel being spaced apart upward from the topsheet as the distal portions of the leak-barrier cuffs are raised up so that the middle portion of the partition forms a barrier against bodily wastes between the topsheet and the panel.

The article further comprises an elastically stretchable spacer extending in the transverse direction being interposed in a stretched state between the topsheet and the panel, the spacer having transversely opposite ends bonded to the side edges of the panel and a portion defined between the transversely opposite side edges so that, under a contractile force of the spacer, the transversely opposite ends are drawn toward each other in the transverse direction of the article while the intermediate region of the panel is spaced apart upward from the topsheet in an upward convex circular arc extending in the transverse direction and the middle portion of the partition forms the barrier against bodily wastes between the topsheet and the panel.

According to a second aspect of the present invention, there is provided a disposable wearing article configured by a front waist region, a rear waist region, a crotch region extending between these two waist regions, longitudinally opposite end portions extending across the respective waist regions in a transverse direction and transversely opposite side portions extending between the front and rear waist regions in a longitudinal direction, the article comprising a liquid-pervious topsheet facing a wearer's skin, a liquid-impervious backsheet facing away a wearer's skin, a pair of liquid-impervious leak-barrier cuffs laid on the topsheet and extending between the front and rear waist regions and a liquid-absorbent core interposed between the top- and backsheets and extending between the front and rear waist regions wherein the leak-barrier cuffs have proximal portions bonded to the opposite side portions of the article so as to extend in the longitudinal direction, distal portions extending in the longitudinal direction and normally biased to rise up above the topsheet and longitudinally opposite end portions collapsed in the transverse direction and bonded to the longitudinally opposite end portions of the article in such a collapsed state and wherein stretchable elastic members extending in the longitudinal direction are contractibly bonded to the distal portions of the leak-barrier cuffs.

The article according to the present invention in the second aspect comprises a skin-contactable panel extending between the leak-barrier cuffs in the transverse direction being laid on the topsheet in the front waist region and a front half of the crotch region divided by a transverse center line bisecting a longitudinal dimension of the article, at least in the front half of the crotch region, and a partition interposed between the topsheet and the panel extends between the leak-barrier cuffs in the transverse direction in a vicinity of the transverse center line; and the panel having transversely opposite side edges bonded to the distal portions of the leak-barrier cuffs and an intermediate region defined between the side edges, and the partition having an upper edge bonded to the panel, a lower edge bonded to the topsheet and a middle portion folded at least into two in a thickness direction of the article, so that the middle portion of the partition forms a barrier against bodily wastes between the topsheet and the panel.

The present invention in the first and second aspects may include preferred embodiments as follow:

The panel is formed from at least one water-absorbent sheet.

The panel is formed from at least one water-absorbent sheet and an absorbent core material wrapped with the water-absorbent sheet and wherein the absorbent core material is at least one of an absorbent core and a foam material containing therein a plurality of cells.

The panel is formed from at least one water-absorbent sheet facing the wearer's skin, a liquid-impervious sheet facing away from the wearer's skin and an absorbent core material interposed between the water-absorbent sheet and the liquid-impervious sheet wherein the absorbent core material is at least one of the absorbent core and a foam material containing therein a plurality of cells.

As long as the disposable wearing article according to the present invention is put on the wearer's body, a dimension by which the transversely opposite side edges of the skin-side panel is reduced and the intermediate region of the panel is spaced apart upward from the topsheet in an upward convex circular arc-shape extending in the transverse direction as the crotch region of the wearer compresses the crotch region of the article inward as viewed in the transverse direction of the article. At the same time, the intermediate region of the partition extending between the panel and the topsheet is unfolded to rise in the thickness direction of the article so that the intermediate region of the partition forms the pocket-like barrier tapered from the crotch region toward the front waist region and thereby prevent loose passage from moving into the front half of the crotch region and even into the front waist region. The article of such an arrangement ensured that the genital organ of the wearer is kept in contact with the panel describing the circular arc above the topsheet and thus the genital organ is reliably spaced from the topsheet. In this way, there is no anxiety that the genital organ might be soiled with loose passage. The barrier against loose passage formed by the middle portion of the partition reliably prevents loose passage from moving into the front half of the crotch region and even into the front waist region and thereby reliably protects the genital organ from soil with loose passage even when loose passage spreads on the topsheet.

In the case of the article that the intermediate region of the panel is bonded to the distal portions of the leak-barrier cuffs at least at transversely opposite ends of an inner end of the intermediate region adjacent the transverse center line, the intermediate region of the panel is spaced apart upward from the topsheet as the distal portions of the leak-barrier cuffs are raised up so that the middle portion of the partition forms a barrier against bodily wastes tapered from the crotch region toward the front waist region between the topsheet and the panel. In the case of this article also, a dimension by which the transversely opposite side edges of the panel is reduced and the intermediate region of the panel is spaced apart upward from the topsheet in an upward convex circular arc-shape projecting above the distal portions of the respective leak-barrier cuffs and extending in the transverse direction as the crotch region of the wearer compresses the crotch region of the article inward as viewed in the transverse direction of the article. In this way, the genital organ in contact with the panel can be reliably spaced from the topsheet and thereby the genital organ can be reliably protected from soil with loose passage. Furthermore, the middle portion of the partition forms the barrier against bodily wastes and thereby reliably can prevent loose passage from moving into the front half of the crotch region and even into the front waist region even when loose passage spreads on the topsheet.

In the case of the article including an elastically stretchable spacer extending in the transverse direction is interposed in a stretched state between said topsheet and said panel, under a contractile force of the spacer, the transversely opposite end portions are drawn toward each other in the transverse direction of the article while the middle portion of the partition extending between the topsheet and the panel is unfolded to rise in the thickness direction of the article and this middle portion of the partition forms the barrier against bodily wastes tapered from the crotch region toward the front waist region. In the case of this article also, a dimension by which the transversely opposite side edges of the panel is reduced and the intermediate portion of the panel is reliably spaced apart upward from the topsheet in an upward convex circular arc-shape as the crotch region of the wearer compresses the crotch region of the article inward as viewed in the transverse direction of the article. In this way, the genital organ in contact with the panel can be reliably spaced apart from the topsheet and thereby the genital organ can be reliably protected from soil with loose passage. Furthermore, the middle portion of the partition forms the barrier against bodily wastes and thereby reliably can prevent loose passage from moving into the front half of the crotch region and even into the front waist region even when loose passage spreads on the topsheet.

In the case of the article that the transversely opposite side edges of the panel are bonded to the distal portions of the respective leak-barrier cuffs, as the distal portions of the respective leak-barrier cuffs rise up above the topsheet, both these side edges and the intermediate portion of the panel are spaced apart upward form the topsheet and the middle portion of the partition extending between the topsheet and the panel is unfolded and raised in the thickness direction of the article as the portions of the respective leak-barrier cuffs rise up above the topsheet. As a result, the middle portion of the partition forms the pocket-like barrier tapered from the crotch region toward the front waist region. In this article also, a dimension by which the transversely opposite side edges of the panel is reduced and the intermediate portion of the panel is reliably spaced apart upward from the topsheet in an upward convex circular arc-shape projecting above the distal portions of the respective leak-barrier cuffs as the crotch region of the wearer compresses the crotch region of the article inward as viewed in the transverse direction of the article. In this way, the genital organ in contact with the panel can be reliably spaced apart from the topsheet and thereby the genital organ can be reliably protected from soil with loose passage. Furthermore, the middle portion of the partition forms the barrier against bodily waste and thereby reliably can prevent loose passage from moving into the front half of the crotch region and even into the front waist region even when loose passage spreads on the topsheet.

In the case of the article having the panel formed from at least one water-absorbent sheet, such water-absorbent sheet can absorb urine discharged onto the article and thereby prevent feces from being mixed with urine. In this way, it can be avoided that feces might be fluidized and the wearer's skin might be soiled with such fluidized feces.

In the case of the article having the panel formed from a water-absorbent sheet and an absorbent core material wrapped with the water-absorbent sheet, urine discharged onto the panel is absorbed through the water-absorbent sheet by the absorbent core material and contained therein. In this way, a large amount of urine can be absorbed by the panel. With this article also, it can be avoided that feces might be mixed with urine to be fluidized and the wearer's skin might be soiled with such fluidized feces.

In the case of the article having the panel formed from the water-absorbent sheet, a liquid-impervious sheet and an absorbent core interposed between these sheets, urine discharged onto the panel is absorbed through the water-absorbent sheet by the absorbent core and contained therein so that a large amount of urine may be absorbed by the panel. With this article, it is unlikely that the amount of urine once having been absorbed by the panel might permeate the liquid-impervious sheet and reach the topsheet. In this way, a large amount of urine can be absorbed by the panel. With this article also, it can be avoided that feces might be mixed with urine to be fluidized and the wearer's skin might be contaminated with such fluidized feces.

DETAILED DESCRIPTION OF THE PREFERRED EMBODIMENTS

Details of a disposable wearing article according to the present invention will be more fully understood from the description given hereunder with reference to the accompanying drawings.

Figure 1:
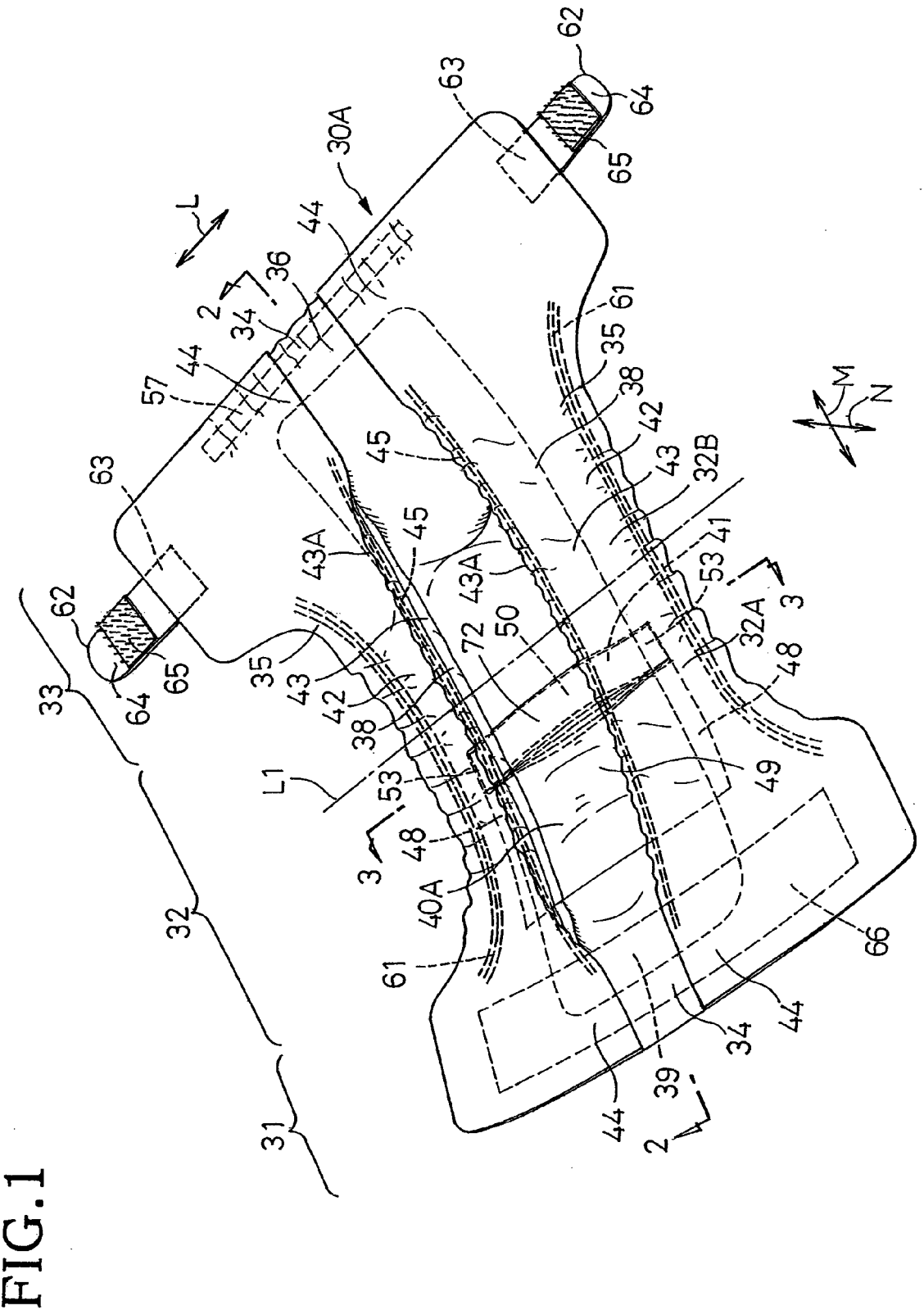
FIG. 1 is a perspective view showing a typical embodiment of a disposable wearing article according to the invention.
Figure 2:
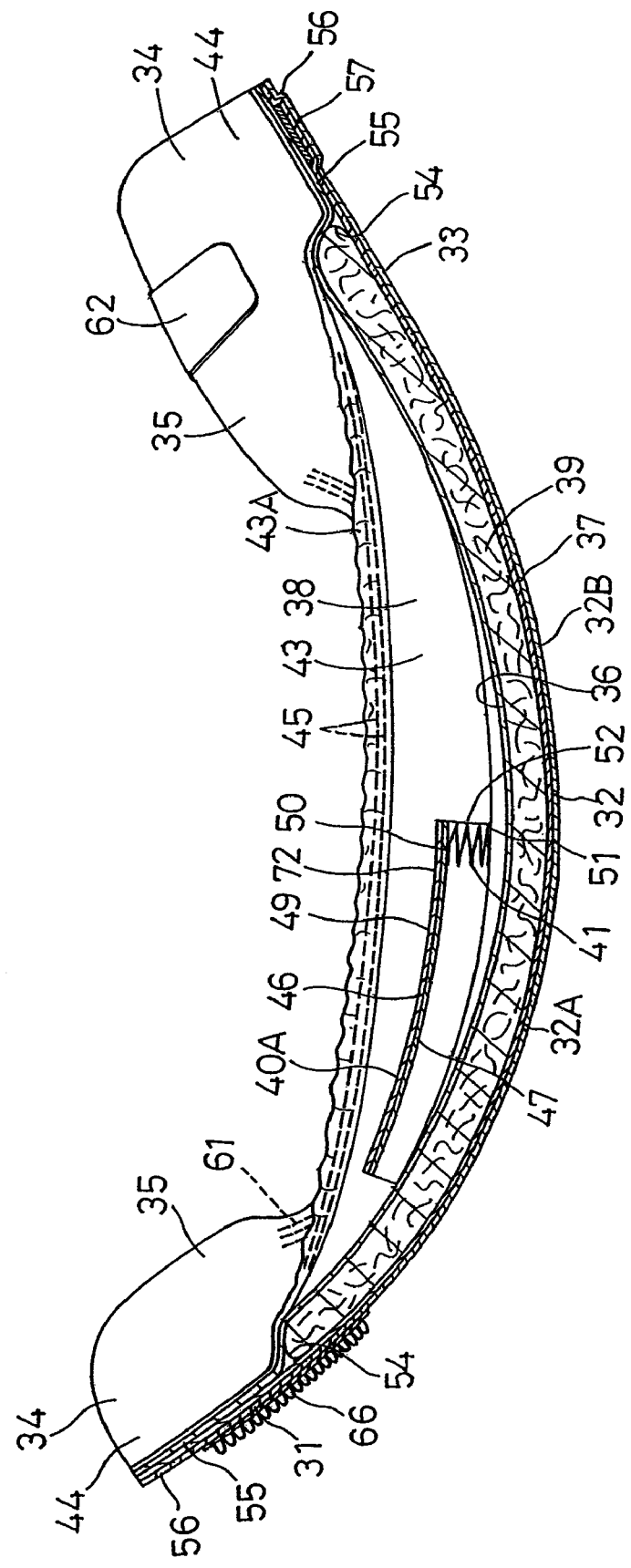
FIG. 2 is a sectional view taken along the line 2-2 in FIG. 1.
Figure 3:
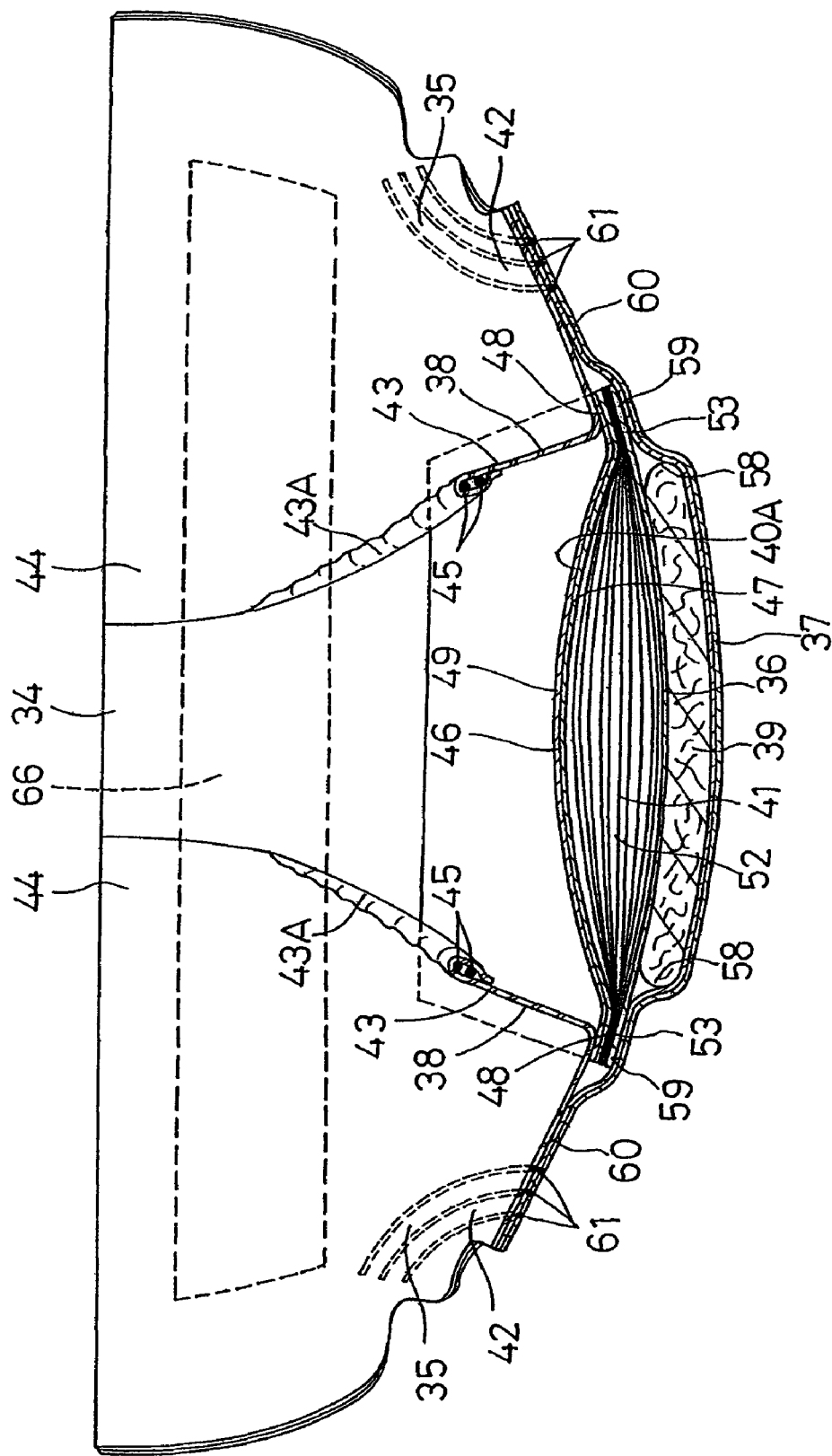
FIG. 3 is a sectional view taken along the line 3-3 in FIG. 1.

FIG. 1 is a perspective view showing a disposable wearing article 30A as a typical embodiment of the invention, FIG. 2 is a sectional view taken along the line 2-2 in FIG. 1 and FIG. 3 is a sectional view taken along the line 3-3 in FIG. 1. In FIG. 1, a transverse direction is indicated by an arrow L, a longitudinal direction is indicated by an arrow M and a thickness direction is indicated by an arrow N.

The article 30A is configured by a front waist region 31, a rear waist region 33, a crotch region 32 extending between these two waist regions 31, 33, longitudinally opposite end portions 34 extending across the front and rear waist regions 31, 33 in a transverse direction and transversely opposite side portions 35 extending between the longitudinally opposite end portions 34 in a longitudinal direction. The wearing article 30A comprises a liquid-pervious topsheet 36 facing the wearer's skin, a liquid-impervious backsheet 37 facing away the wearer's skin, a pair of liquid-impervious leak-barrier cuffs 38 lying on the outer surface of the topsheet 36 and extending in the longitudinal direction and a liquid-absorbent core 39 interposed between the top- and backsheets 36, 37 and bonded to the inner surface of these sheets 36, 37. The core 39 is placed so as to occupy the front and rear waist regions 31, 33 as well as the crotch region 32 except the longitudinal opposite end portions 34 and the transversely opposite side portions 35. The transversely opposite side portions 35 of the crotch region 32 respectively describe circular arcs which are convex transversely inward of the article 30A and thus article 30A has an hourglass-like planar shape. Between the leak-barrier cuffs 38, there are provided a skin-contactable panel 40A and a liquid-impervious partition 41 both extending in the transverse direction.

The topsheet 36 is formed from a hydrophilic fibrous nonwoven fabric and the backsheet 37 is formed from a composite nonwoven fabric composed of two hydrophobic fibrous nonwoven fabric layers laminated on each other. Each of the leak-barrier cuffs 38 is formed from a repellent treated hydrophobic nonwoven fabric. The core 39 comprises a mixture of particulate or fibrous super-absorbent polymers and fluff pulp fibers or a mixture of particulate or fibrous super-absorbent polymers, fluff pulp fibers and thermoplastic synthetic resin fibers, in any case, compressed to a given thickness. The core 39 is entirely wrapped with a tissue paper (not shown) in order to prevent the core 39 from getting out of its initial shape.

Each of the leak-barrier cuffs 38 has a proximal portion 42 integrally bonded to the associated one of the transversely opposite side portions 35 and extending in the longitudinal direction, a distal portion 43 extending in the longitudinal direction in parallel to the proximal portion 42 and normally biased to rise up above the topsheet 36 and longitudinally opposite end portions 44 collapsed inward in the transverse direction of the article 30A and integrally bonded in such a collapsed state to the longitudinally opposite end portions 34 of the article 30A. Both the proximal portion 42 and the distal portion 43 extend between the longitudinally opposite end portions 34 of the article 30A. A stretchable elastic member 45 extending in the longitudinal direction is secured to the distal portion 43 in the vicinity of its upper edge 43A while the elastic member 45 is stretched at a predetermined ratio in the longitudinal direction. Contraction of the elastic members 45 associated with the pair of the leak-barrier cuffs 38 causes the article 30A to be curved with the topsheet 36 inside and at the same time causes the distal portions 43 to be left to contract. Consequentially the distal portions 43 of the leak-barrier cuffs 38 rise up above the topsheet and form barriers against bodily wastes. The distal portions 43 of the respective leak-barrier cuffs 36 thus rising up above the topsheet 36 reliably prevent bodily wastes from leading sideways out from the article 30A.

The panel 40A having a generally rectangular shape which is relatively long in the transverse direction is laid on the outer surface of the topsheet 36 in a front half area 32A of the crotch region 32 divided by a transverse center line L1 bisecting a longitudinal dimension of the article 30A. The panel 40A comprises a pair of hydrophilic nonwoven fabric layers 46, 47 laminated on each other, which are water-absorbent. These nonwoven fabric layers 46, 47 have respective surfaces opposed to each other intermittently and integrally bonded together by means of adhesive (not shown). The panel 40A has transversely opposite side edges 48 lying on the transversely opposite side portions 35 of the article 30A and an intermediate region 49 extending between side edges 48.

The partition 41 is laid in the vicinity of the transverse center line L1, i.e., an inner end 72 of the intermediate region 49 of the panel 40A adjacent the transverse center line L1. The partition 41 is interposed between the topsheet 36 and the panel 40A. The partition 41 is made of a liquid-impervious plastic film. The partition 41 has upper and lower edges 50, 51 extending in the transverse direction, a middle region 52 extending in the thickness direction of the article 30A between the upper and lower edges 50, 51 and transversely opposite side edges 53 lying on the transversely opposite side portions 35 of the article 30A. The upper edge 50 is integrally bonded to the inner surface of the panel 40A and the lower edge 36 is integrally bonded to the topsheet 36. The partition 41 is folded in three in the thickness direction of the article 30A so as to have a zigzag cross-section as will be seen in FIG. 2.

The longitudinally opposite end portions 34 of the article 30A are respectively formed from longitudinally opposite end portions 55, 56 of the top- and backsheets 36, 37 extending outward beyond longitudinally opposite ends 54 of the core 39 and the longitudinally opposite end portions 44 of the leak-barrier cuffs 38. Along the longitudinally opposite end portions 34, the end portions 55, 56 of the top- and backsheets 36, 37 are placed upon the end portions 44, the respective inner surfaces of the top- and backsheets 36, 37 are integrally bonded one to another and the outer surface of the topsheet 36 is integrally bonded to the respective inner surfaces of the leak-barrier cuffs 38. A tape-like waist-surrounding elastic member 57 extending in the transverse direction is contractibly attached to the end portion 34 of the rear waist region 33. This waist-surrounding elastic member 57 is interposed between the end portion 55 of the topsheet 36 and the end portion 56 of the backsheet 37 and secured to the respective inner surfaces of these sheets 36, 37 with the elastic member 57 stretched at a predetermined ratio in the transverse direction.

The transversely opposite side portions 35 of the article 30A are respectively formed from transversely opposite side edges 59, 60 of the top- and backsheets 36, 37 and the proximal portions 42 of the leak-barrier cuffs 38. Along the transversely opposite side portions 35, the side edge portions 59 of the topsheet 36 extend outward slightly beyond transversely opposite side edges 58 of the core 39, the side edge portions 60 of the backsheet 37 and the respective proximal portions 42 of the leak-barrier cuffs 38 extend further outward beyond the side edge 59. Along the side portions 35, the side edge portions 59, 60 of the top- and backsheets 36, 37 and the proximal portions 42 of the leak-barrier cuffs 38 are placed one upon another, the respective inner surfaces of the top- and backsheets 36, 37 are integrally bonded together, and the inner and outer surfaces of the top- and backsheets 36, 37 and the respective inner surfaces of the leak-barrier cuffs 38 are permanently bonded together.

A plurality of leg-surrounding elastic members 61 generally extending in the longitudinal direction are contractibly attached to the side portions 35 of the article 30A. The leg-surrounding elastic members 61 are interposed between those two nonwoven fabric layers constituting the backsheet 37 and secured to the mutually opposed surfaces of these nonwoven fabric layers while the elastic members 61 are stretched at a predetermined ratio in a longitudinal direction thereof. The transversely opposite side edges 48 of the panel 40A are interposed between the side edge portions 59 of the topsheet 36 and the proximal portions 42 of the leak-barrier cuffs 38 and integrally bonded to the inner and outer surfaces of the topsheet 36 and the barrier cuffs 38. The transversely opposite side edge portions 53 of the partition 41 are interposed between the side edge portions 59 of the topsheet 36 and the side edges 48 of the panel 40A and integrally bonded to the outer surface of the topsheet 36 and to the inner surface of the panel 40A.

Flexible tape fasteners 62 made of a plastic film strip are respectively attached to the side portions 35 of the rear waist region 33. These tape fasteners 62 respectively have proximal portions 63 and distal portions 64 both extending in the transverse direction. The proximal portions 63 are interposed between the side edge portions 60 of the backsheet 37 and the proximal portions 42 of the leak-barrier cuffs 38 and integrally bonded to the respective inner surfaces of the backsheet 37 and the cuffs 38. Male mechanical fasteners 65 provided with a plurality of hooks are attached to the inner surfaces of the respective distal portions 64. The respective distal portions 64 are folded inward as viewed in the transverse direction of the article 30A and temporarily fixed to the respective outer surfaces of the proximal portions 42 of the associated leak-barrier cuffs 38 by means of the hooks (See FIG. 2). It should be understood that the mechanical fasteners 65 provided on the respective distal portions 64 may be replaced by pressure-sensitive adhesive applied on these distal portions 64.

The front waist region 31 is provided with a flexible target tape strip 66 on which the distal portions 64 of the respective tape fasteners 62 are destined to be detachably anchored. The target tape strip 66 is formed from a plastic film strip and a female mechanical fastener comprising a plurality of loops. The target tape strip 66 is shaped in a rectangle being relatively long in the transverse direction and integrally bonded to the outer surface of the backsheet 37. When it is desired to coat the distal portions 64 of the respective tape fasteners 62 with pressure-sensitive adhesive, plastic film is used as a stock material for the target tape strip 66.

Figure 4:
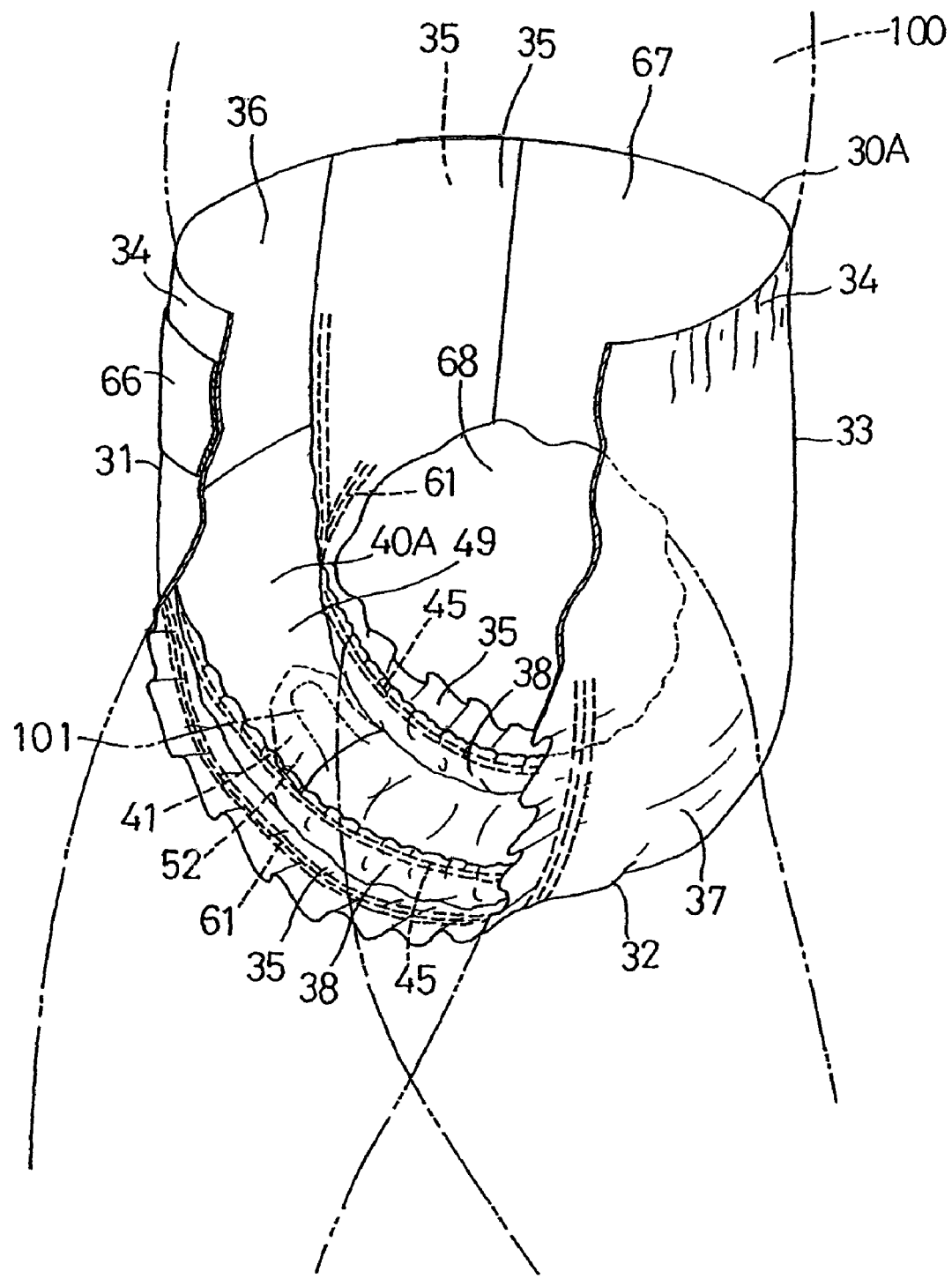
FIG. 4 is a perspective view showing the article of FIG. 1 as put on the wearer's body.

FIG. 4 is a perspective view showing the article 30A of FIG. 1 as put on the article wearer's body, in which the front and rear waist regions 31, 33 are illustrated as partially cut away on one side of the waist. To put the article 30A on the wearer's body, the opposite side portions 35 of the rear waist region 33 are placed on the opposite side portions 35 of the front waist region 31 from the outside, then the distal portions 64 of the respective tape fasteners 62 are pressed against the target tape strip 66 to bring the hooks in engagement with the loops and thereby the distal portions 64 are anchored on the target tape strip 66. Thus the front and rear waist regions 31, 33 are connected with each other and thereupon the article 30A is formed with a waist-hole 67 and a pair of leg-holes 68.

After the wearing article 30A has been put on the wearer's body, the buttocks of the wearer 100 is in contact with the outer surface of the topsheet 36 and the penis 101 (genital organ) of the wearer 100 is in contact with the outer surface of the intermediate region 49 of the panel 40A. The crotch region 32 of the article 30A is normally squeezed between the thighs of the wearer 100 inward as viewed in the transverse direction and thereby the distance between the side edges 48 of the panel 40A is reduced. Consequentially, the intermediate region 49 rises above the topsheet 36 so as to describe an upward convex circular arc extending in the transverse direction and to be spaced apart upward from the outer surface of the topsheet 36. As the intermediate region 49 is spaced apart upward from the outer surface of the topsheet 36, the middle region 52 of the partition 41 extending between the topsheet 36 and the panel 40A is unfolded in the thickness direction of the article 30A and thereby the middle region 52 raises itself in the thickness direction of the article 30A so that the middle region 52 may form a pocket-like barrier tapered from the crotch region 32 toward the front waist region 31. As long as the article 30A is put on the wearer's body, the panel 40A raising itself above the topsheet 36 so as to describe the circular arc slings the partition 41 upward and keeps the middle region 52 of the partition 41 in a raised state. Therefore, it is unlikely that the middle region 52 might unintentionally collapse and the partition 41 might no more function as the barrier. A significant part of urine discharged onto the article 30A is absorbed by the panel 40A while loose passage discharged onto the rear half 32B of the crotch region 32 as well as onto the rear waist region 33 is absorbed and contained by the core 39 through the topsheet 36. A remaining part of urine which has not been absorbed by the panel 40A is absorbed and contained by the core 39 through the topsheet 36 in the front half 32A of the crotch region 32 as well as in the front waist region 31.

After the article 30A has been put on the wearer's body, the penis 101 of the wearer 100 is in contact with the outer surface of the panel 40A but spaced apart upward from the outer surface of the topsheet 36 as the intermediate region 49 of the panel 40A is spaced apart upward from the outer surface of the topsheet 36, so the penis 101 is no more brought in contact with the topsheet 36. The middle region 52 of the partition 41 forms the pocket-like barrier adapted to prevent loose passage from further flowing into the front half 32A of the crotch region 32 and even into the front waist region 31 even when loose passage discharged onto the rear half 32B of the crotch region 32 as well as onto the rear waist region 33 spreads on the outer surface of the topsheet 36. Even if a large amount of loose passage is discharged on the article 30A, such a large amount of loose passage is reliably received by the pocket-like barrier formed by the partition 41 and there is no anxiety that such loose passage might flow beyond the partition 41 to the outer surface of the panel 40A.

The article 30A is thus adapted to protect the penis 101 from contact with the topsheet 36 and to restrict the movement of loose passage. It is thereby ensured that the penis 101 is reliably protected from soil with loose passage. In addition, the partition 41 prevents urine discharged onto the article 30A from flowing into the rear half 32B of the crotch region 32 and further into the rear waist region 33 and also prevents loose passage from moving into the front half 32A of the crotch region 32 and further into the front waist region 31. In this way, there is no anxiety that feces might be mixed with urine to be fluidized and thereby contaminate the skin of the wearer 100.

Figure 5:
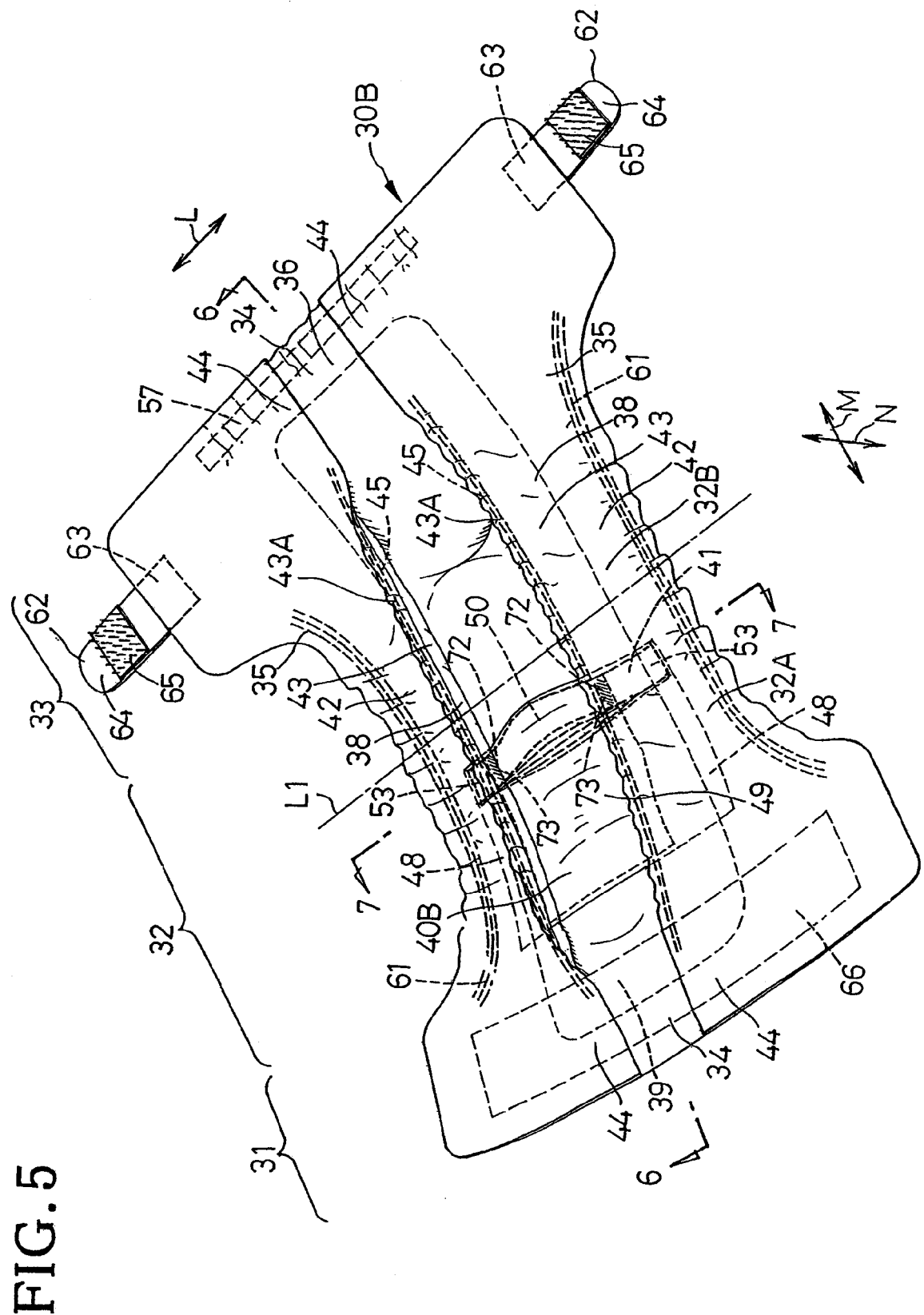
FIG. 5 is a perspective view showing one preferred embodiment of the disposable wearing article according to the invention.
Figure 6:
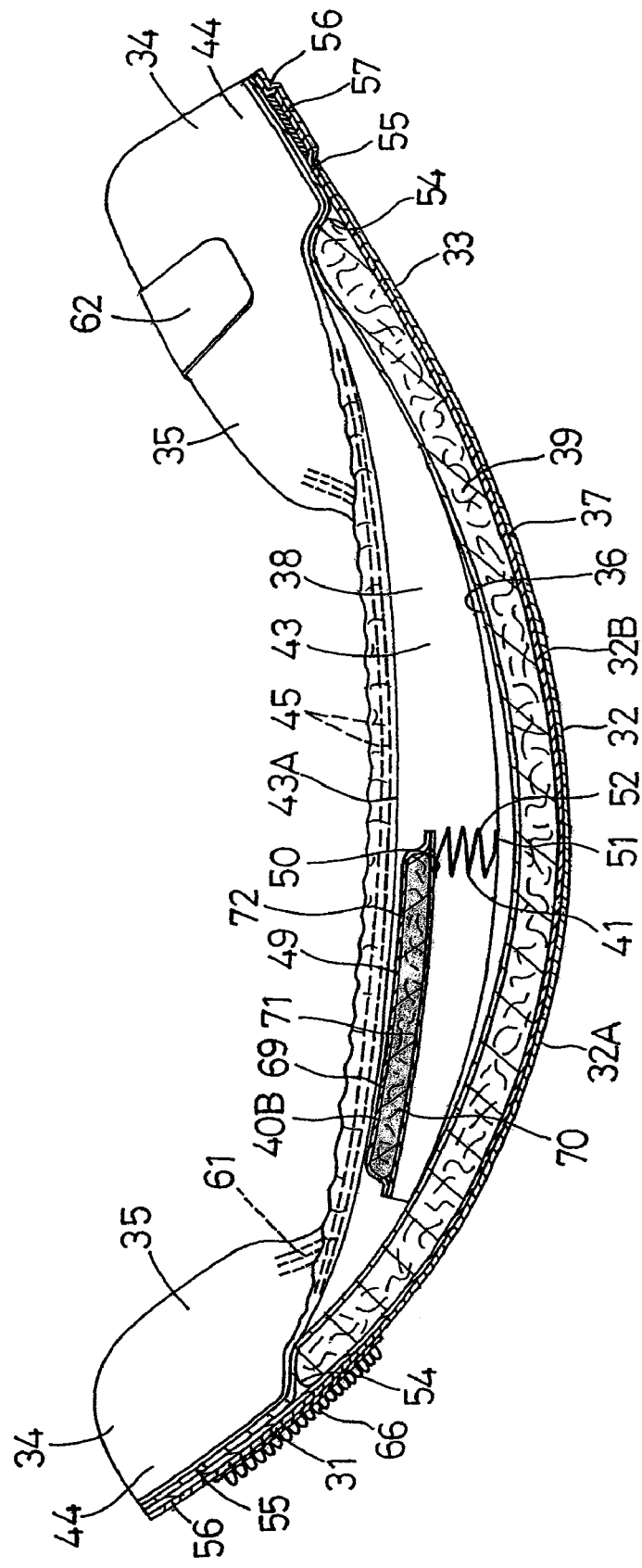
FIG. 6 is a sectional view taken along the line 6-6 in FIG. 5.
Figure 7:
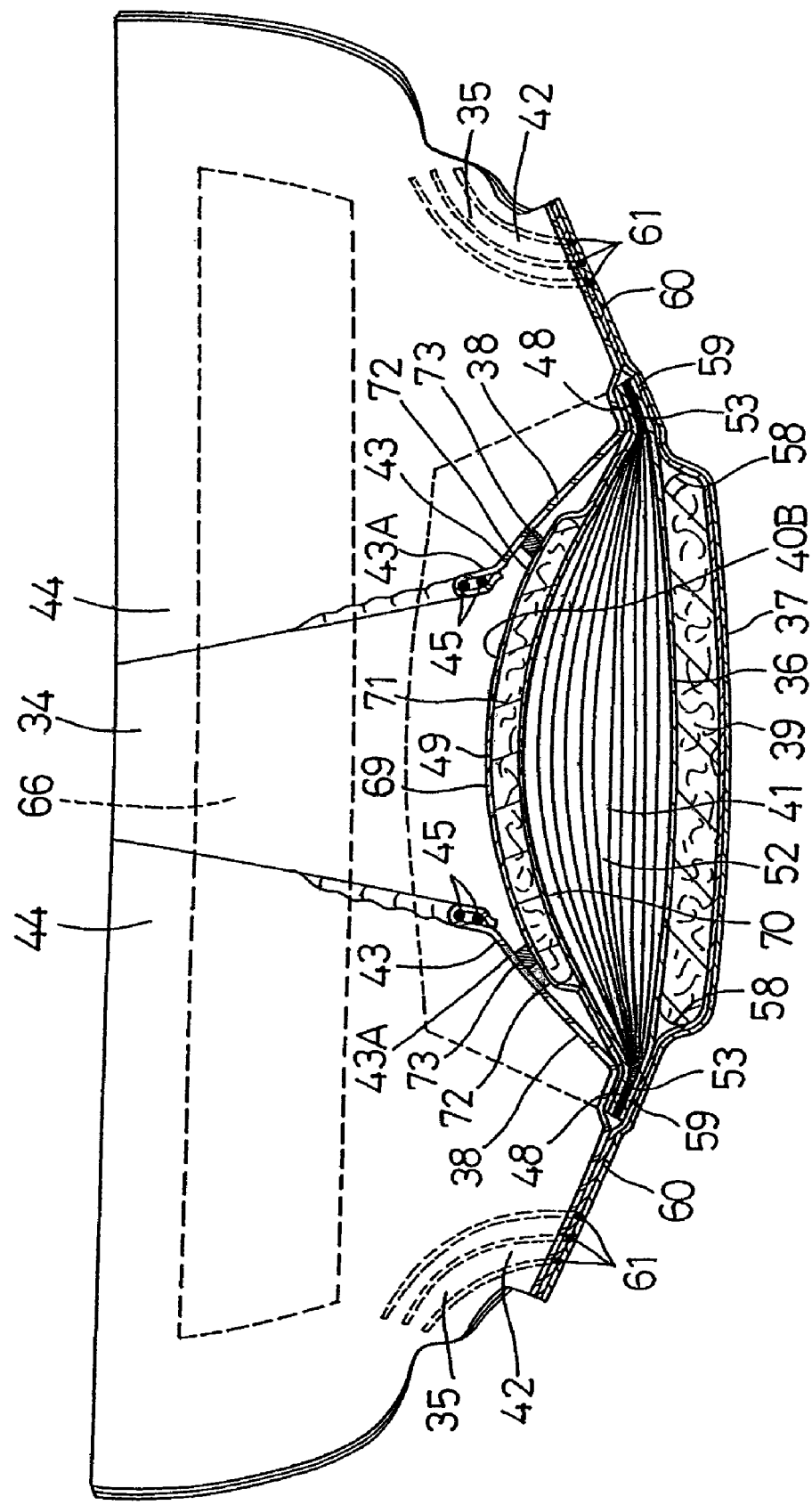
FIG. 7 is a sectional view taken along the line 7-7 in FIG. 5.

FIG. 5 is a perspective view showing a disposable article 30B as one preferred embodiment of the invention, FIG. 6 is a sectional view taken along the line 6-6 in FIG. 5 and FIG. 7 is a sectional view taken along the line 7-7 in FIG. 5. In FIG. 5, a transverse direction is indicated by an arrow L, a longitudinal direction is indicated by an arrow M and a thickness direction is indicated by an arrow N.

The article 30B is similar to the article 30A except that a panel 40B is formed by first and second fibrous nonwoven fabric flayers 69, 70 and a liquid-absorbent core 71 entirely covered with these nonwoven fabric layers 69, 70 and an intermediate region 49 of this panel 40B is integrally bonded to distal portions 43 of respective leak-barrier cuffs 38. The components similar to those in the article 1A are denoted by the similar reference numerals and the description of the arrangement similar to that in the article 1A will be omitted here.

The panel 40B having a generally rectangular shape which is relatively long in the transverse direction is laid on the outer surface of the topsheet 36 in a front half area 32A of the crotch region 32 divided by a transverse center line L1 bisecting a longitudinal dimension of the article 30B. The panel 40B comprises a first hydrophilic nonwoven fabric layer 69 which is water-absorbent, a second hydrophilic fibrous nonwoven fabric layer 70 which is water-absorbent and a liquid-absorbent core 71 interposed between the first and second fibrous nonwoven fabric layers 69, 70. These nonwoven fabric layers 69, 70 have respective portions extending outward beyond a peripheral edge of the core 71 placed upon and integrally bonded to each other. The core 71 is intermittently bonded to the respective inner surfaces of these nonwoven fabric layers 69, 70 by means of adhesive (not shown). The core 71 comprises the same mixture as that in the case of the core 39 entirely wrapped with a tissue paper (not shown). The core 71 has a stiffness higher than those of the first and second fibrous nonwoven fabric layers 69, 70.

The panel 40B has transversely opposite side edges 48 lying on the transversely opposite side portions 35 of the article 30B and an intermediate region 49 extending between the side edges 48. The side edges 48 are respectively formed from the first and second fibrous nonwoven fabric layers 69, 70 except the core 71. The inner end 72 of the intermediate region 49 lying adjacent the transverse center line L1 has transversely opposite ends integrally bonded to the distal portions 43, preferably, the upper edges 43A of the leak-barrier cuffs 38 in the vicinity of the elastic members 45. The transversely opposite ends of the inner end 72 are integrally bonded to the respective distal portions 43 of the leak-barrier cuffs 38 by means of adhesive 73. The intermediate region 49 is raised above the topsheet 36 and spaced apart upward from the outer surface of the topsheet 36 as the distal portions 43 of the leak-barrier cuffs 38 are elastically biased to rise. Without departing from the scope of the invention, the side edges of the intermediate region 49 may be integrally bonded along the full length of these edges to the distal portions 43, preferably, the upper edges 43A of the leak-barrier cuffs 38 in the vicinity of the elastic members 45. The side edges 48 of the panel 40B are interposed between the side edge portions 59 of the topsheet 36 and the side edge portions 42 of the respective leak-barrier cuffs 38 and integrally bonded to the inner and outer surfaces of the topsheet 36 and the cuffs 38.

Figure 8:
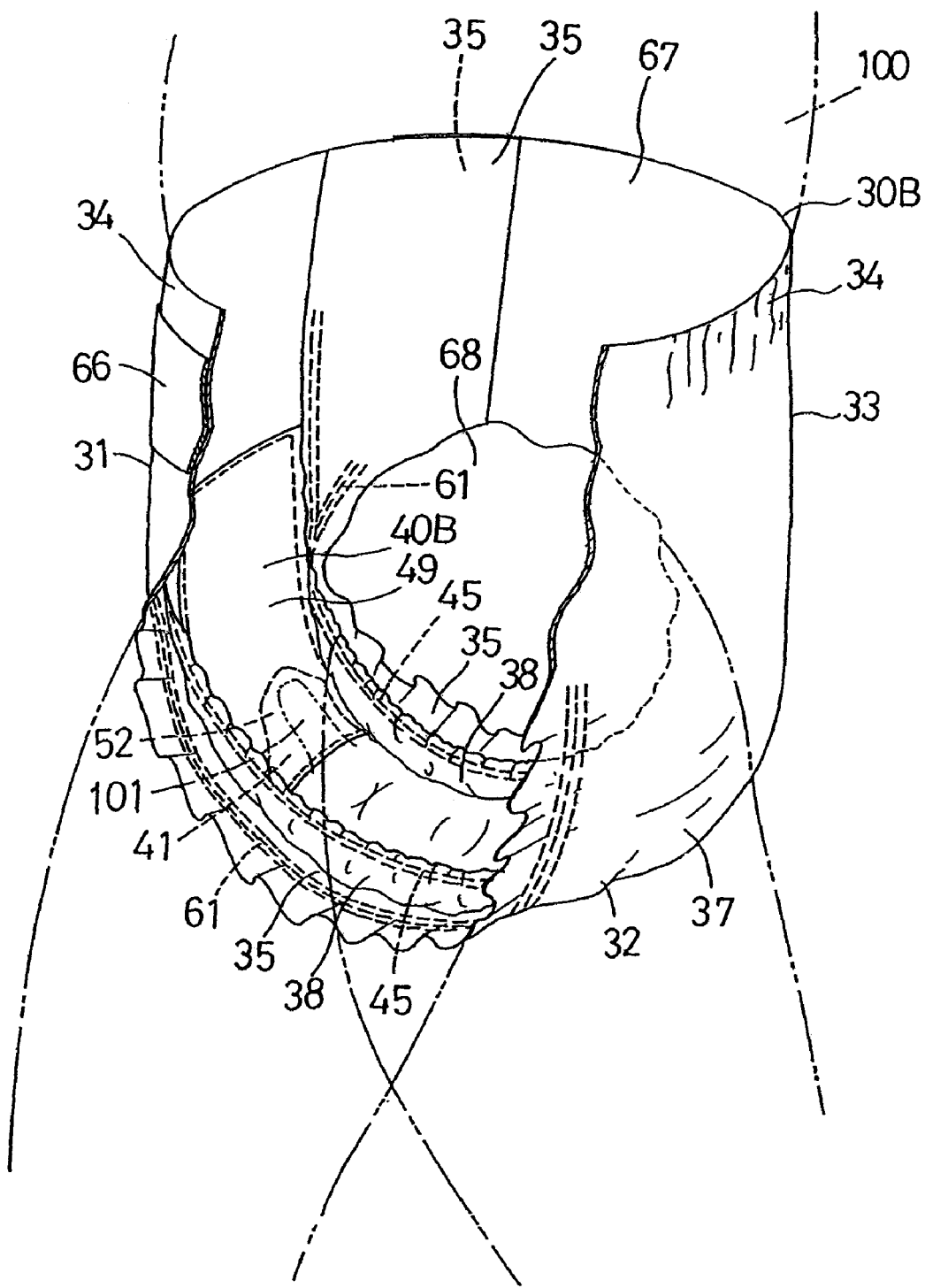
FIG. 8 is a perspective view showing the article of FIG. 5 as put on the article wearer's body.

FIG. 8 is a perspective view showing the article 30B of FIG. 5 as put on the wearer's body, in which the side edges 35 are cut away on one side of the waist. Sequential procedures to put the article 30B on the wearer's body are the same as in the case of the article 30A and the description thereof will be omitted here. After the article 30B has been put on the wearer's body, the buttock of the wearer 100 is in contact with the outer surface of the topsheet 36 and the penis 101 of the wearer 100 is in contact with the outer surface of the intermediate region 49 of the panel 40B. The intermediate region 49 is integrally bonded to the distal portion 43 of the liquid-barrier cuffs 38 and therefore more easily rises above the topsheet 36 so as to describe an upward convex circular arc extending in the transverse direction and to be spaced upward from the outer surface of the topsheet 36.

The article 30B thus allows urine discharged thereonto to be absorbed through the first fibrous nonwoven fabric layer 69 by the core 71 as well as the core 39 and to be retained therein so that a large amount of urine can be absorbed by the panel 40B.

Figure 9:
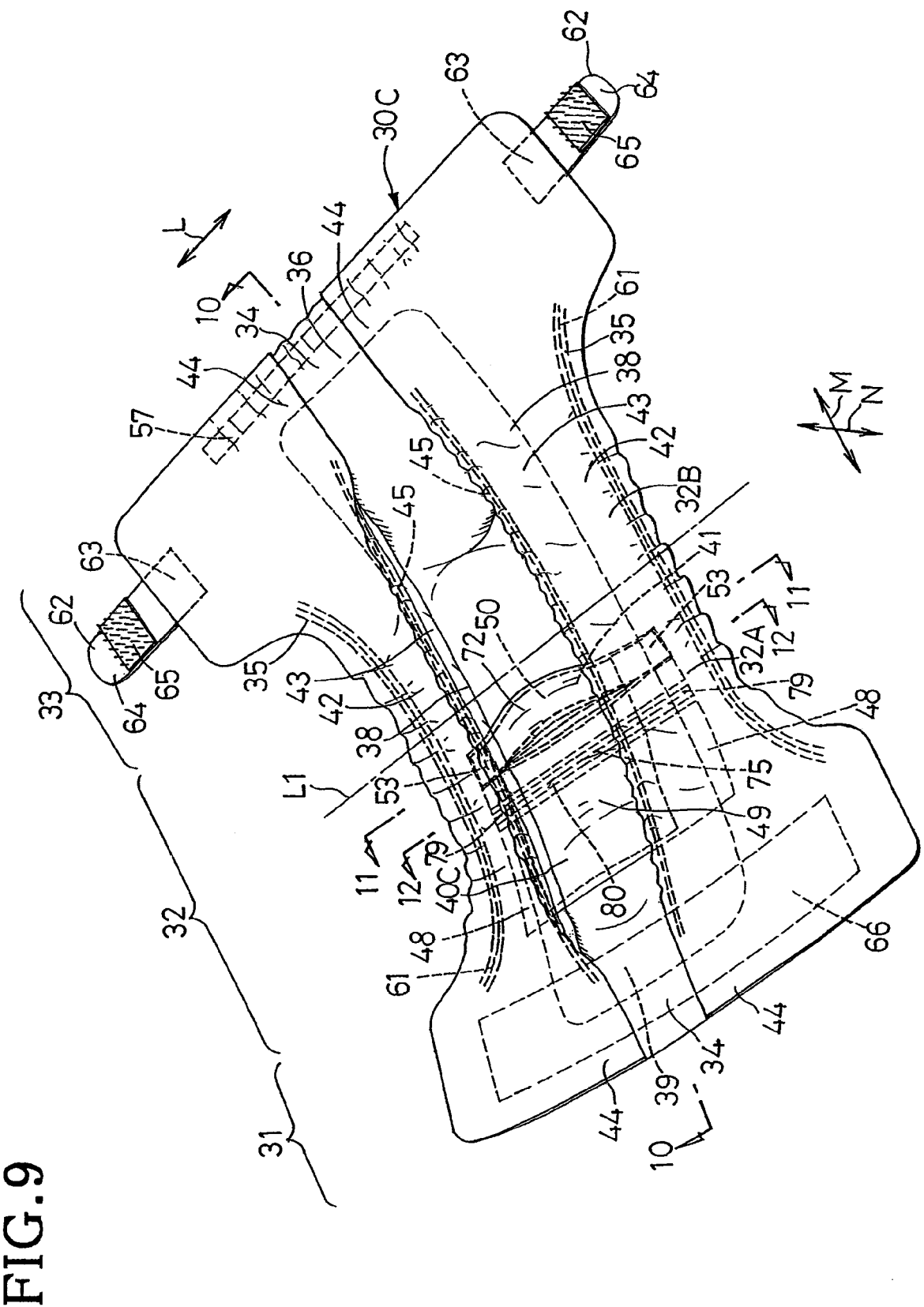
FIG. 9 is a perspective view showing another preferred embodiment of the disposable wearing article according to the invention.
Figure 10:
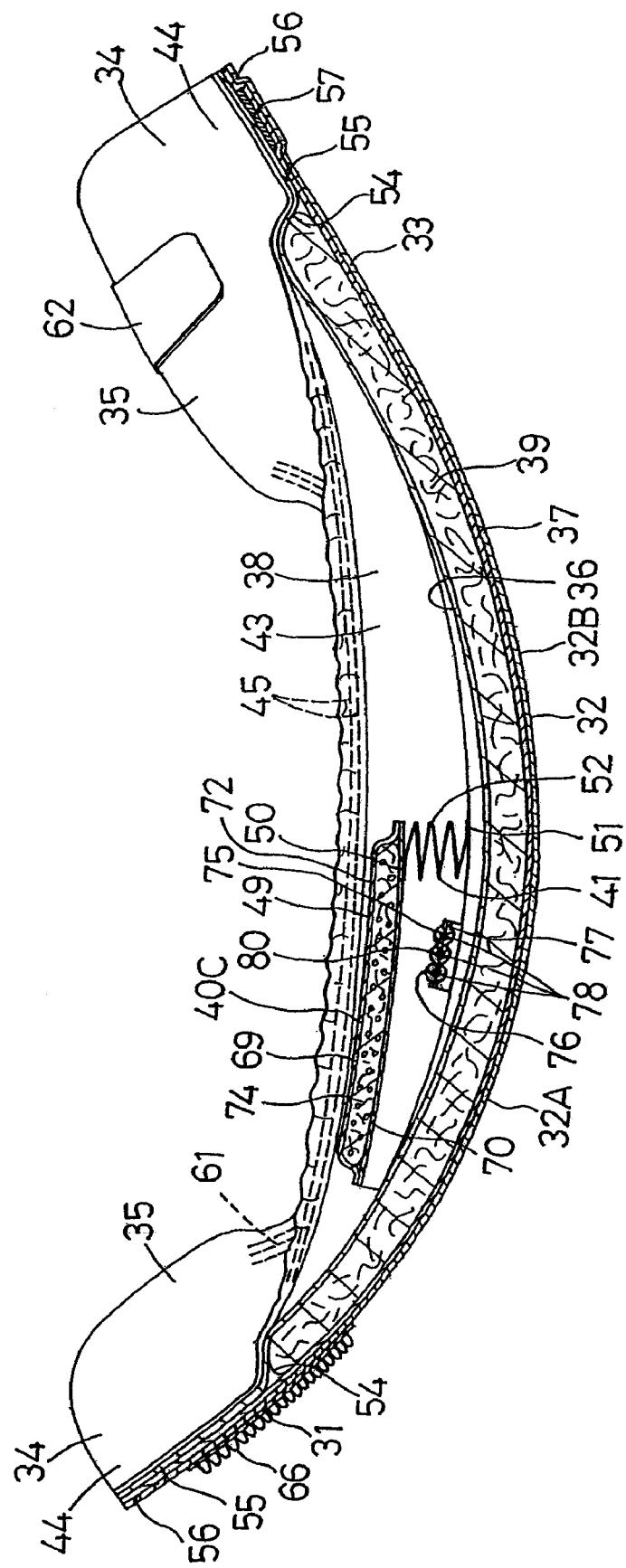
FIG. 10 is a sectional view taken along the line 10-10 in FIG. 9.
Figure 11:
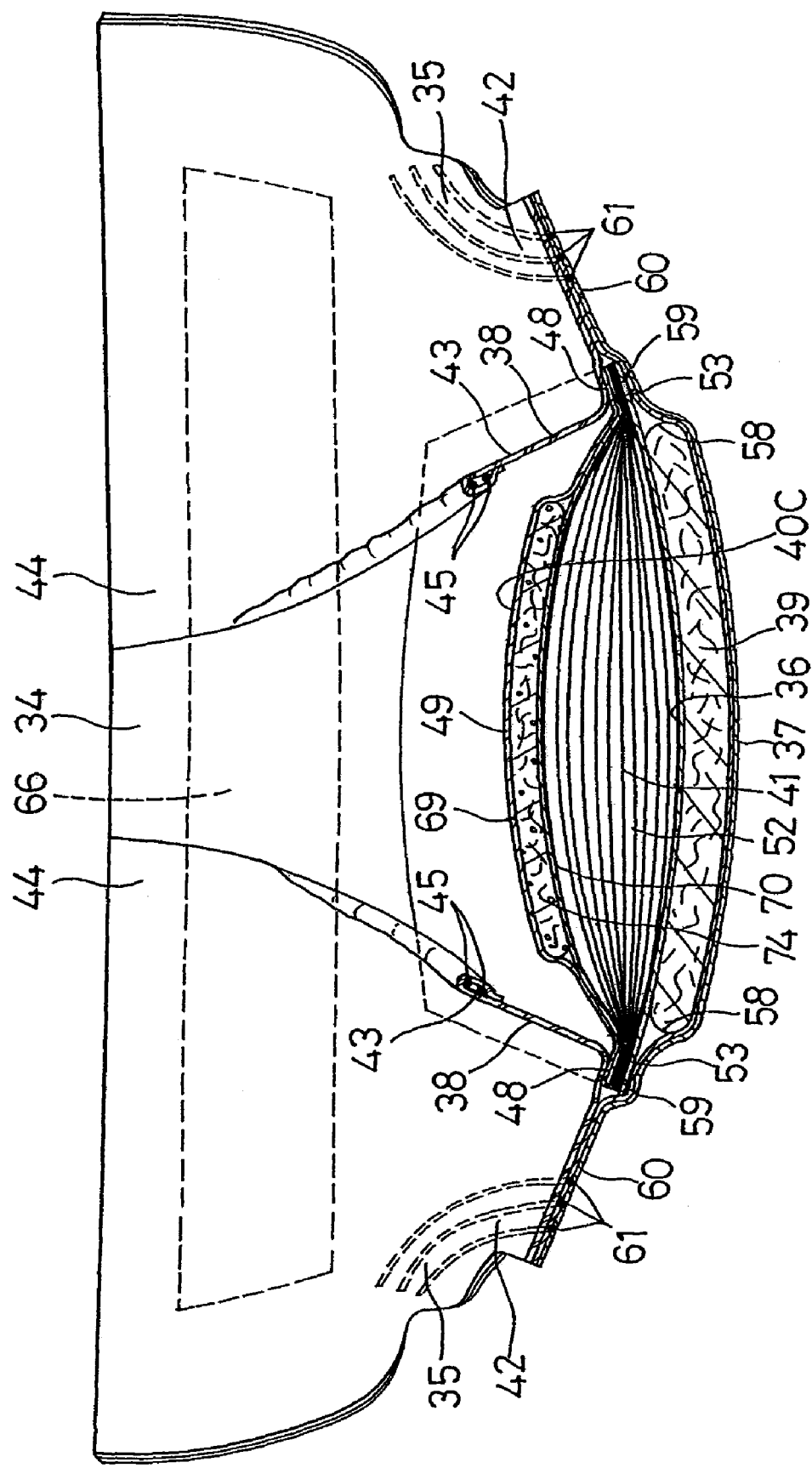
FIG. 11 is a sectional view taken along the line 11-11 in FIG. 9.
Figure 12:
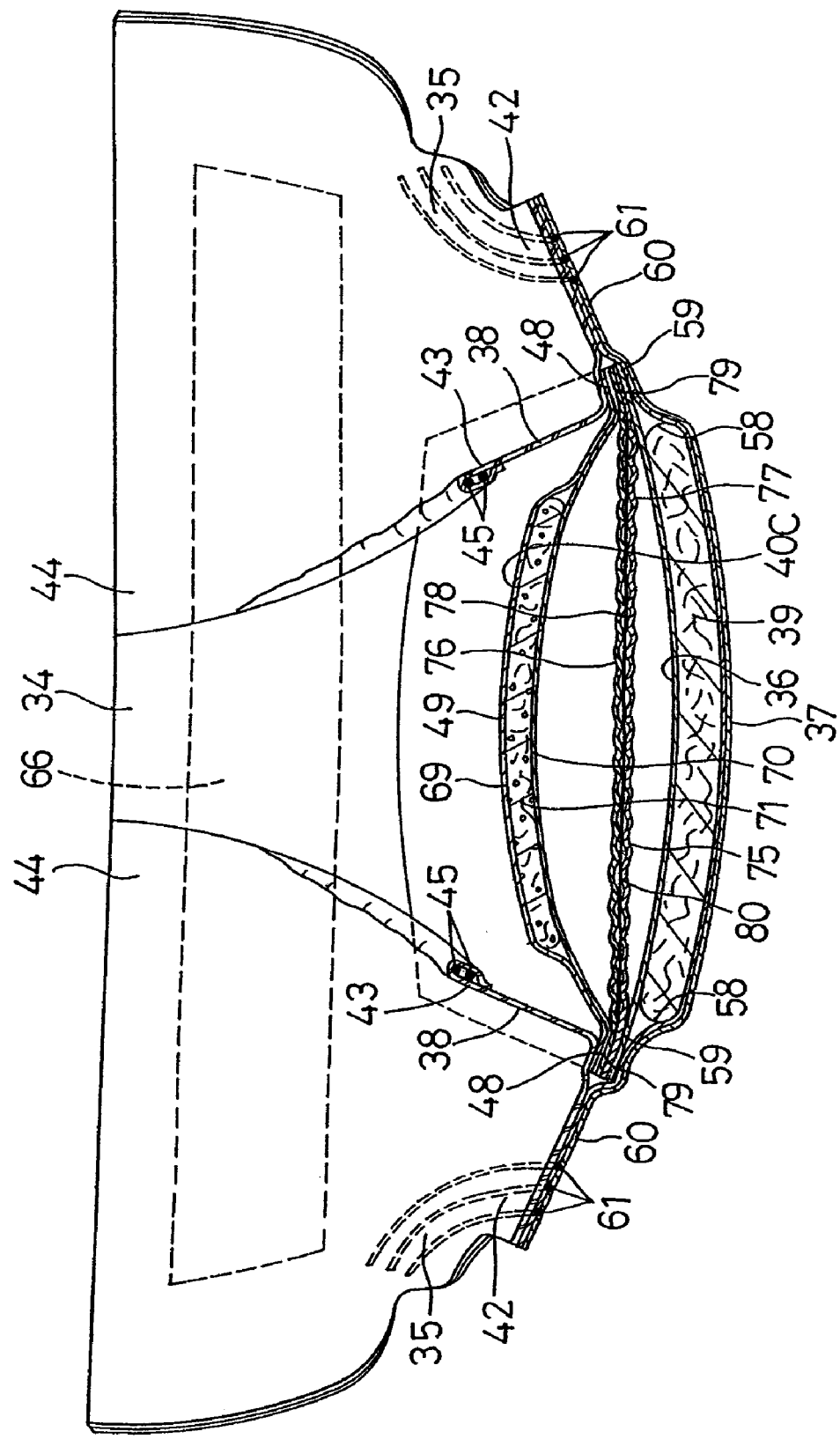
FIG. 12 is a sectional view taken along the line 12-12 in FIG. 9.

FIG. 9 is a perspective view showing a disposable wearing article 30C as another preferred embodiment of the invention, FIG. 10 is a sectional view taken along the line 10-10 in FIG. 9, FIG. 11 is a sectional view taken along the line 11-11 in FIG. 9 and FIG. 12 is a sectional view taken along the line 12-12 in FIG. 9. In FIG. 9, a transverse direction is indicated by an arrow L, a longitudinal direction is indicated by an arrow M and a thickness direction is indicated by an arrow N.

The article 30C is similar to the article 30A except that that a panel 40C is formed from first and second fibrous nonwoven fabric flayers 69, 70 and an absorbent urethane foam 74 entirely covered with these nonwoven fabric layers 69, 70 and a spacer 75 interposed between the topsheet 36 and the panel 40C so as to extend in the transverse direction. The components similar to those in the article 1A are denoted by the similar reference numerals and the description of the arrangement similar to that in the article 1A will be omitted here.

The panel 40C having a generally rectangular shape which is relatively long in the transverse direction is laid on the outer surface of the topsheet 36 in a front half area 32A of the crotch region 32 divided by a transverse center line L1 bisecting a longitudinal dimension of the article 30C. The panel 40C comprises a first hydrophilic nonwoven fabric layer 69 (which is water-absorbent) facing the wearer's skin, a second hydrophilic fibrous nonwoven fabric layer 70 (which is water-absorbent) facing away from the wearer's skin and an absorbent urethane foam 74 interposed between the first and second fibrous nonwoven fabric layers 69, 70. These nonwoven fabric layers 69, 70 have respective portions extending outward beyond a peripheral edge of the absorbent urethane foam 74 placed upon and permanently bonded to each other. The absorbent urethane foam 74 contains therein a plurality of open cells. The absorbent urethane foam 74 is intermittently bonded to the respective inner surfaces of these nonwoven fabric layers 69, 70 by means of adhesive (not shown). It should be understood that absorbent core materials to used is not limited to the absorbent urethane foam 74 but may be selected from the group consisting of cellulose sponge, nylon sponge and styrene foam.

The panel 40C has transversely opposite side edges 48 lying on the transversely opposite side portions 35 of the article 30C and an intermediate region 49 extending between these side edges 48. The side edges 48 are respectively formed from the first and second fibrous nonwoven fabric layers 69, 70 except the absorbent urethane foam 74. The side edges 48 of the panel 40C are interposed between the side edge portions 59 of the topsheet 36 and the side portions 42 of the leak-barrier cuffs 38 and integrally bonded to the inner and outer surfaces of the topsheet 36 and the cuffs 38.

As will be seen in FIG. 12, the spacer 75 is interposed between the topsheet 36 and the panel 40C and laid in the vicinity of the partition 41, i.e., on the side of the inner end portion B2 of the intermediate region 49. The spacer 75 is formed from a pair of hydrophilic or hydrophobic fibrous nonwoven fabric layers 76, 77 and a plurality of stretchable elastic members 78 extending in the transverse direction and contractibly attached to these fibrous nonwoven fabric layers 76, 77. These elastic members 78 are interposed between the fibrous nonwoven fabric layers 76, 77 and intermittently bonded to the mutually opposed surfaces of these fibrous nonwoven fabric layers 76, 77 by means of adhesive (not shown) while the elastic members 78 are stretched at a predetermined ratio in the transverse direction. The spacer 75 has transversely opposite ends 79 laid in the vicinity of the transversely opposite side portions 35 of the article 30C and a stretchable/contractible intermediate region 80 defined between the opposite side portions 35. The ends 79 are interposed between the side edge portions 59 of the topsheet 36 and the side edges 48 of the panel 40C and integrally bonded to the outer surface of the topsheet 36 as well as to the inner surface of the panel 40C while the spacer 75 is stretched at a predetermined ratio in the transverse direction. A contractile force of the spacer 75 which has been relieved from the stretch stress causes the transversely opposite side edges 48 to be pulled toward each other in the transverse direction of the article 30C and thereby causes the intermediate region 49 of the panel 40C to rise above the topsheet 36 so as to describe an upward convex circular arc extending in the transverse direction.

Figure 13:
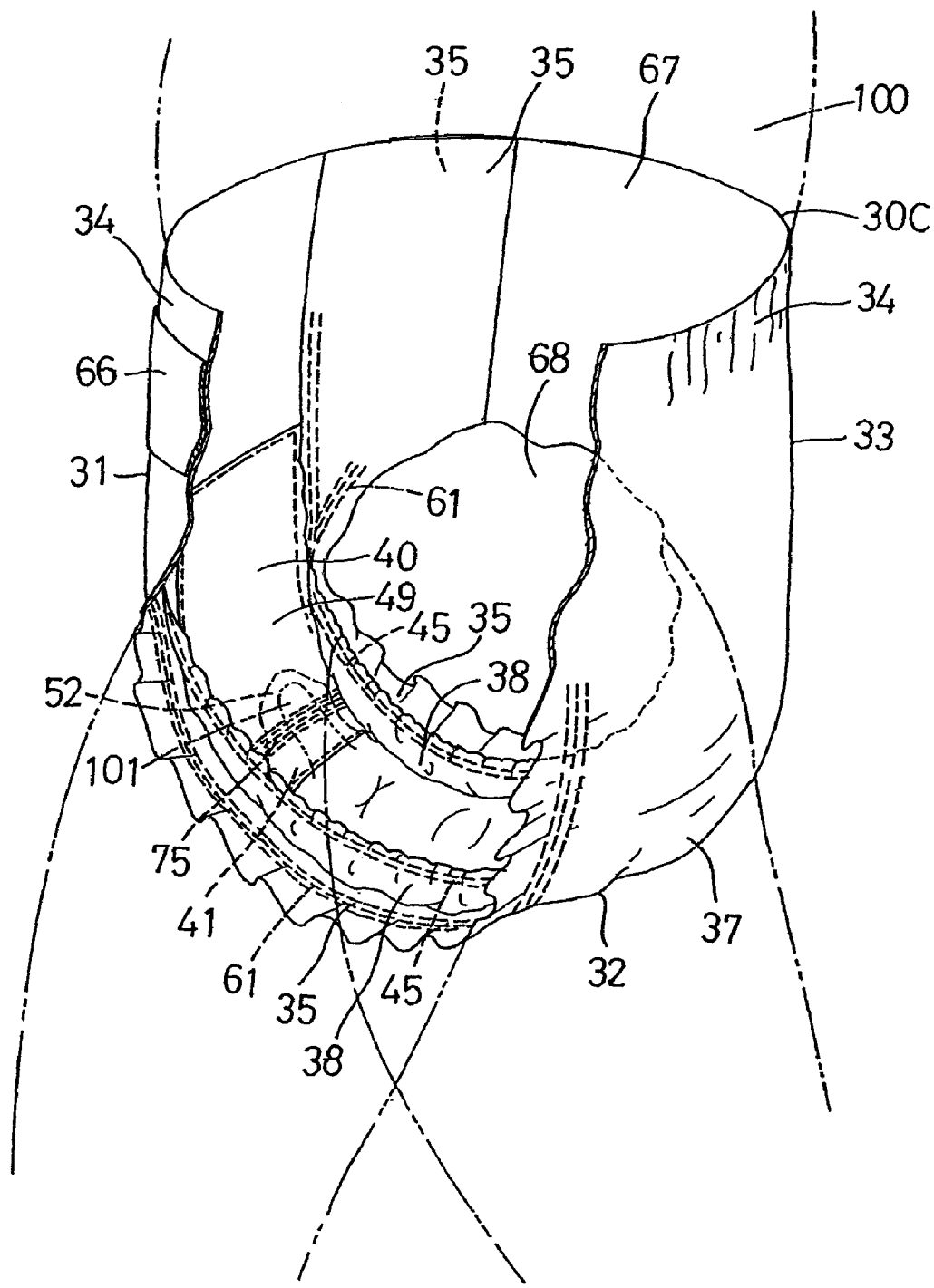
FIG. 13 is a perspective view showing the article of FIG. 9 as put on the wearer's body.

FIG. 13 is a perspective view showing the article 30C of FIG. 9 as put on the wearer's body, in which the front and rear waist regions 31, 33 are illustrated as partially cut away on one side of the waist. Sequential procedures to put the article 30C on the wearer's body are the same as in the case of the article 30A and the description thereof will be omitted here. After the article 30C has been put on the wearer's body, the buttock of the wearer 100 is in contact with the outer surface of the topsheet 36 and the penis 101 of the wearer 100 is in contact with the outer surface of the intermediate region 49 of the panel 40C.

As has already been described, the contractile force of the spacer 75 causes the intermediate region 49 of the panel 40C to rise above the topsheet 36 in the upward convex circular arc-shape. Such an arrangement ensures that the intermediate region 49 rises above the topsheet 36 so as to describe an upward convex circular arc extending in the transverse direction and to be reliably spaced apart upward from the outer surface of the topsheet 36 as the crotch region 32 is squeezed between the thighs of the wearer 100 inward as viewed in the transverse direction. As the intermediate region 49 is spaced apart upward from the outer surface of the topsheet 36, the middle portion 52 of the partition 41 extending between the topsheet 36 and the panel 40C is unfolded in the thickness direction of the article 30C and thereby the middle portion 52 raises itself in the thickness direction of the article 30C so that the middle portion 52 may form a pocket-like barrier tapered from the crotch region 32 toward the front waist region 31. As long as the article 30C is put on the panel 40C raising itself above the topsheet 36 so as to describe the circular arc slings the partition 41 upward and keeps the middle portion 52 of the partition 41 in a raised state. Therefore, it is unlikely that the middle portion 52 might unintentionally collapse and the partition 41 might no more function as the barrier. Urine discharged onto the article 30C is absorbed and contained by the absorbent urethane foam 74 through the first fibrous nonwoven fabric 69 while loose passage discharged onto the rear half 32B of the crotch region 32 as well as onto the rear waist region 33 is absorbed and contained by the core 39 through the topsheet 36. The article 30C allows urine discharged thereonto to be absorbed through the first fibrous nonwoven fabric layer 69 by the absorbent urethane foam 74 and to be contained therein so that a large amount of urine can be absorbed by the panel 40C. The contractile force of the spacer 75 maintains the intermediate region 49 in the upward convex circular arc-shape above the topsheet 36.

Figure 14:
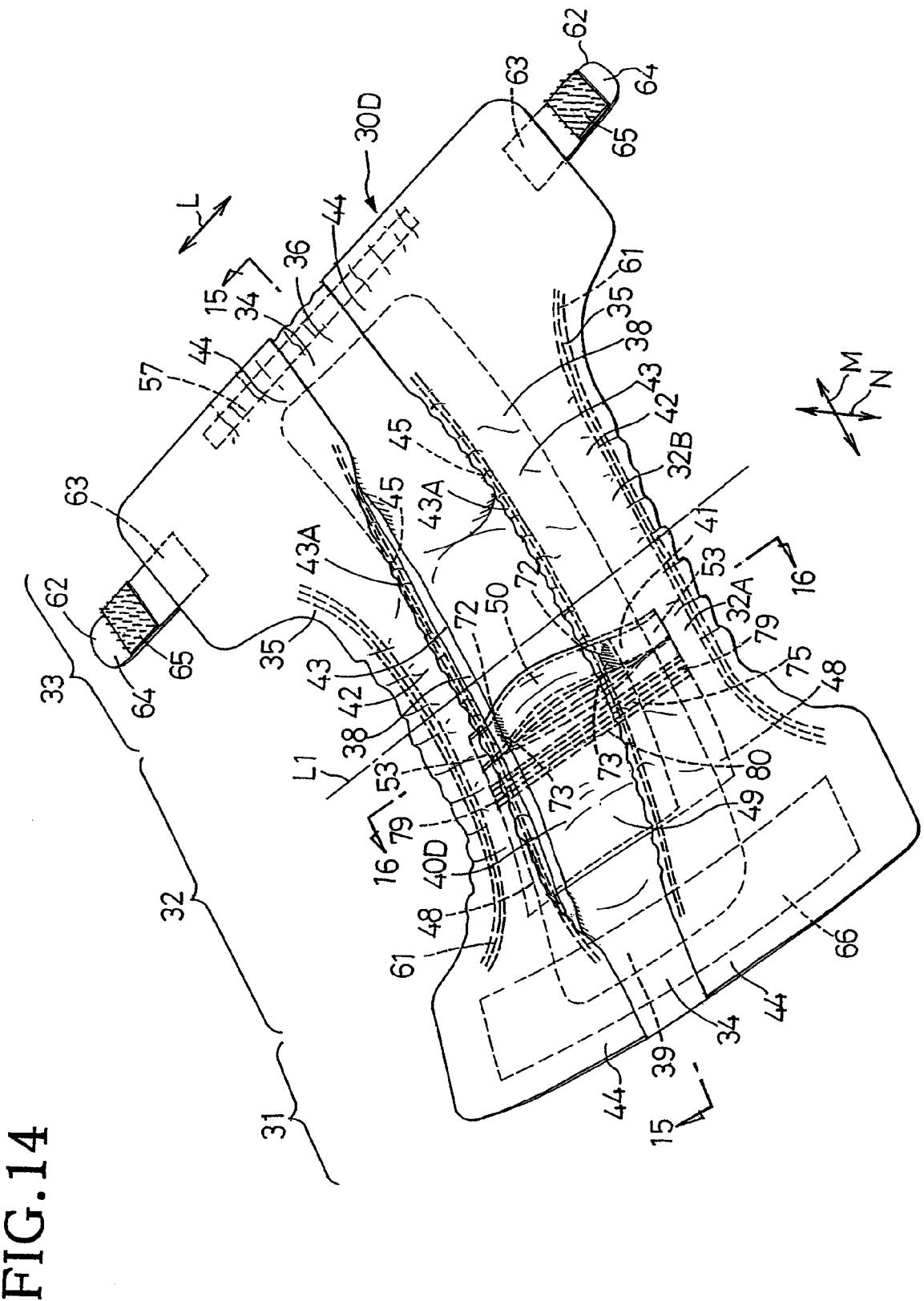
FIG. 14 is a perspective view showing still another preferred embodiment of the disposable wearing article according to the invention.
Figure 15:
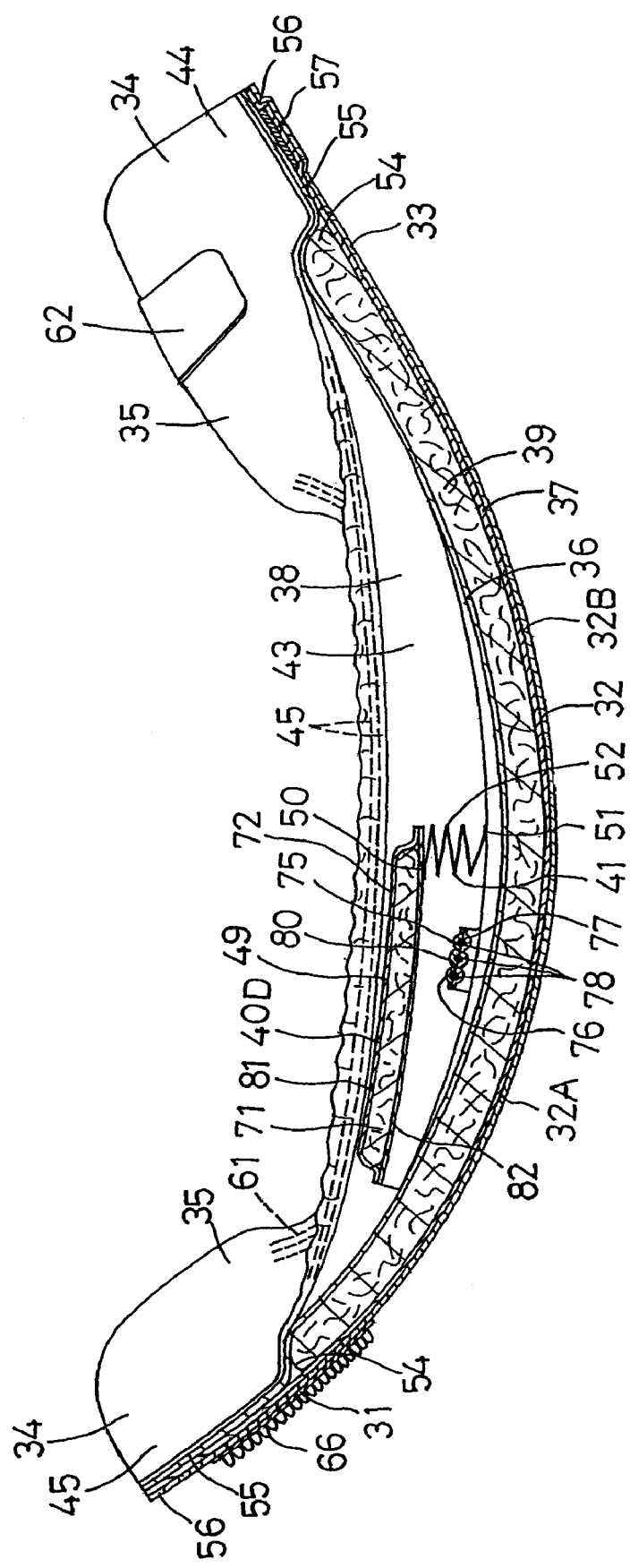
FIG. 15 is a sectional view taken along the line 15-15 in FIG. 14.
Figure 16:
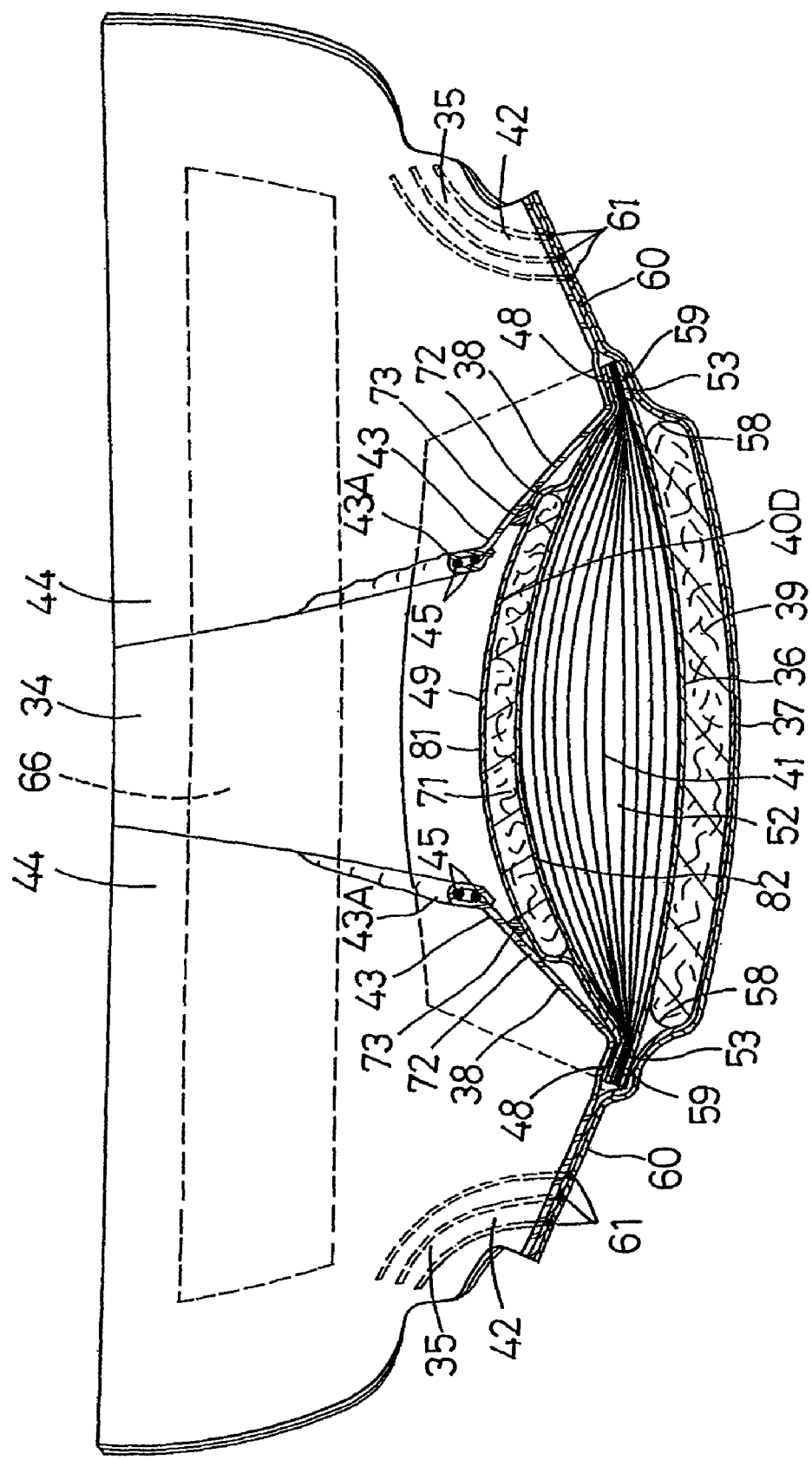
FIG. 16 is a sectional view taken along the line 16-16 in FIG. 14.

FIG. 14 is a perspective view showing a disposable wearing article 30D as still another preferred embodiment of the invention, FIG. 15 is a sectional view taken along the line 15-15 in FIG. 14 and FIG. 16 is a sectional view taken along the line 16-16 in FIG. 14. In FIG. 14, a transverse direction is indicated by an arrow L, a longitudinal direction is indicated by an arrow M and a thickness direction is indicated by an arrow N.

The article 30D is similar to the article 30A except that a panel 40D comprises the hydrophilic fibrous nonwoven fabric layer 81, the liquid-impervious plastic film 82 and the liquid-absorbent core 71 entirely covered with these nonwoven fabric layer 81 and film 82, the intermediate region 49 of the panel 40D is integrally bonded to the distal portions 43 of the respective leak-barrier cuffs 38 and the spacer 75 is interposed between the topsheet 36 and the panel 40D. The components similar to those in the article 1A are denoted the similar reference numerals and the description of the arrangement similar to that in the article 1A will be omitted here.

The panel 40D having a generally rectangular shape which is relatively long in the transverse direction is laid on the outer surface of the topsheet 36 in a front half area 32A of the crotch region 32 divided by a transverse center line L1 bisecting a longitudinal dimension of the article 30D. The panel 40D comprises a hydrophilic nonwoven fabric layer 81 (which is water-pervious) facing the wearer's skin, a hydrophobic plastic film 82 (which is liquid-impervious) facing away from the article wearer's skin and a liquid-absorbent core 71 interposed between the fibrous nonwoven fabric layers 81 and the film 82. These nonwoven fabric layer 81 and film 82 have respective portions extending outward beyond a peripheral edge of the core 71 placed upon and integrally bonded to each other. In the panel 40D, it is possible without departing from the scope of the invention to replace the liquid-impervious plastic film 82 by a hydrophobic fibrous nonwoven fabric. The core 71 is intermittently bonded to the respective inner surfaces of these nonwoven fabric layer 81 and the film 82 by means of adhesive (not shown). The core 71 comprises the same mixture as that constituting the core 39 and entirely wrapped with a tissue paper (not shown). The core 71 has a stiffness higher than those of the nonwoven fabric 81 and the film 82.

The panel 40D has transversely opposite side edges 48 lying on the transversely opposite side portions 35 of the article 30D and an intermediate region 49 extending between these side edges 48. The side edges 48 are respectively formed from the fibrous nonwoven fabric layer 81 and the film 82 except the core 71. The inner end portion 72 of the intermediate region 49 lying adjacent the transverse center line L1 has transversely opposite ends integrally bonded to the distal portions 43, preferably, the upper edges 43A of the leak-barrier cuffs 38 in the vicinity of the elastic members 45. Without departing from the scope of the invention, the transversely opposite side edges of the intermediate region 49 may be entirely bonded to the distal portions 43 of the respective leak-barrier cuffs 38 in the vicinity of the elastic members 45. The side edges 48 of the panel 40D are interposed between the side edge portions 59 of the topsheet 36 and the side portions 42 of the leak-barrier cuffs 38 and integrally bonded to the inner and outer surfaces of the topsheet 36 and the cuffs 38.

The spacer 75 is interposed between the topsheet 36 and the panel 40C and laid in the vicinity of the barrier sheet 41, i.e., on the side of the inner end portion 72 of the intermediate region 49. The spacer 75 is formed from a pair of hydrophilic or hydrophobic fibrous nonwoven fabric layers 76, 77 and a plurality of stretchable elastic members 78 extending in the transverse direction and contractibly attached to these fibrous nonwoven fabric layers 76, 77. These elastic members 78 are interposed between the fibrous nonwoven fabric layers 76, 77 and intermittently bonded to the mutually opposed surfaces of these fibrous nonwoven fabric layers 76, 77 by means of adhesive (not shown) while the elastic members 78 are stretched at a predetermined ratio in the transverse direction. The spacer 75 has transversely opposite ends 79 laid in the vicinity of the transversely opposite side portions 35 of the article 30D and a stretchable/contractible intermediate region 80 defined between the opposite side portions 35. The ends 79 are interposed between the side edges 59 of the topsheet 36 and the side edges 48 of the panel 40D and integrally bonded to the outer surface of the topsheet 36 as well as to the inner surface of the panel 40C while the spacer 75 is stretched at a predetermined ratio in the transverse direction.

In the case of the article 30D, the intermediate region 49 of the panel 40D is spaced apart upward from the outer surface of the topsheet 36 as the distal portion 43 of the respective leak-barrier cuffs 38 rise up above the topsheet 36. In addition, a contractile force of the spacer 75 which has been relieved from the stretch stress causes the transversely opposite side edges 48 to be pulled toward each other in the transverse direction of the article 30D and thereby causes the intermediate region 49 of the panel 40D to rise above the topsheet 36 so as to describe an upward convex circular arc extending in the transverse direction.

Figure 17:
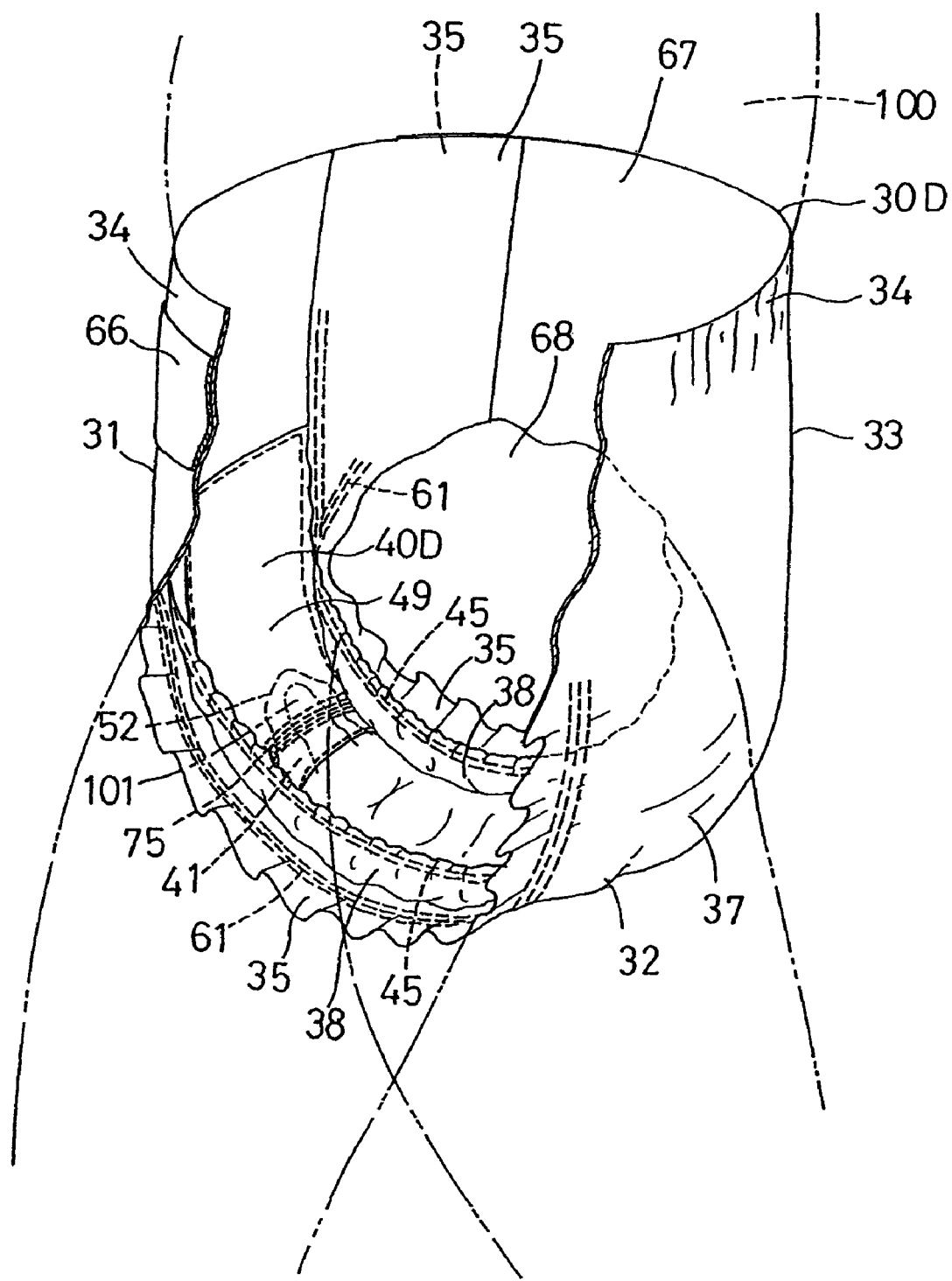
FIG. 17 is a perspective view showing the article of FIG. 14 as put on the wearer's body.

FIG. 17 is a perspective view showing the article 30D as put on the wearer's body, in which the front and rear waist regions 31, 33 are illustrated as partially cut away on one side of the waist. Sequential procedures to put the article 30D on the wearer's body are the same as in the case of the article 30A and the description thereof will be omitted here. After the article 30D has been put on the wearer's body, the buttock of the wearer 100 is in contact with the outer surface of the topsheet 36 and the penis 101 of the wearer 100 is in contact with the outer surface of the intermediate region 49 of the panel 40D.

In the case of the article 30D, as has already been described, the intermediate region 49 of the panel 40D is spaced apart upward from the outer surface of the topsheet 36 as the distal portions 43 of the respective leak-barrier cuffs 38 rise up above the topsheet 36 and, in addition, the contractile force of the spacer 75 causes the intermediate region 49 of the panel 40D to rise above the topsheet 36 in the upward convex circular arc-shape. Such arrangement ensures that the intermediate region 49 rises above the topsheet 36 so as to describe an upward convex circular arc extending in the transverse direction and to be reliably spaced apart upward from the outer surface of the topsheet 36 as the crotch region 32 is squeezed between the thighs of the wearer 100 inward as viewed in the transverse direction. Urine discharged onto the article 30D is absorbed and contained by the core 71 through the fibrous nonwoven fabric 81 while loose passage discharged onto the article 30D is absorbed by the core 39 through the topsheet 36 and then contained therein.

In the article 30D, the urine-impervious film 82 prevents urine from moving to the topsheet 36 and the partition 41 prevents feces from moving to the front half 32A of the crotch region 32 and to the front waist region 31. In this way, there is no anxiety that feces might be mixed with urine to be fluidized and thereby contaminate the skin of the wearer 100. The article 30D thus allows urine discharged thereonto to be absorbed by the core 71 through the fibrous nonwoven fabric layer 81 and to be contained therein so that a large amount of urine can be absorbed by the panel 40D. The contractile force of the spacer 75 maintains the intermediate region 49 in the upward convex circular arc-shape above the topsheet 36.

Figure 18:
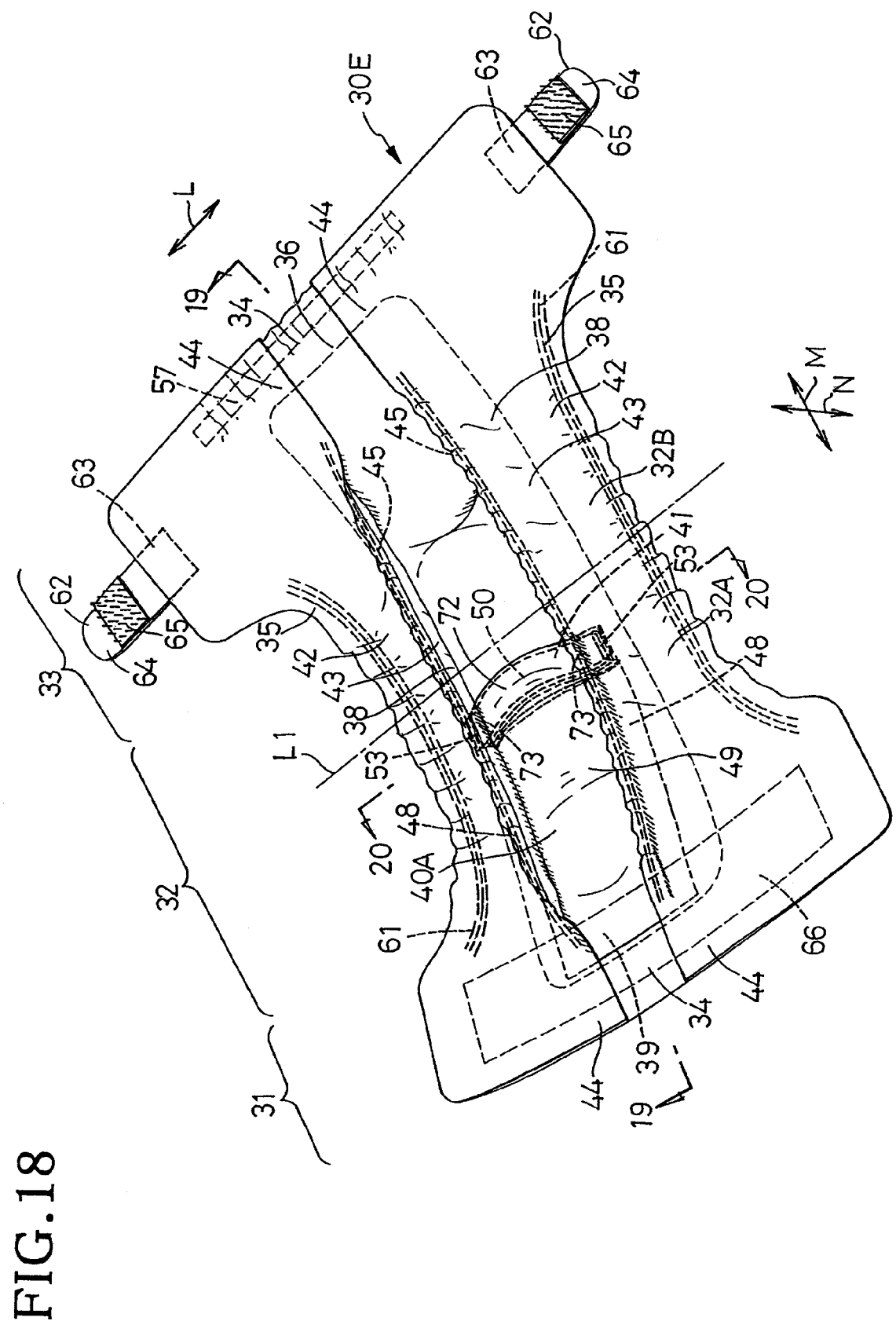
FIG. 18 is a perspective view showing further another preferred embodiment of the disposable wearing article according to the invention.
Figure 19:
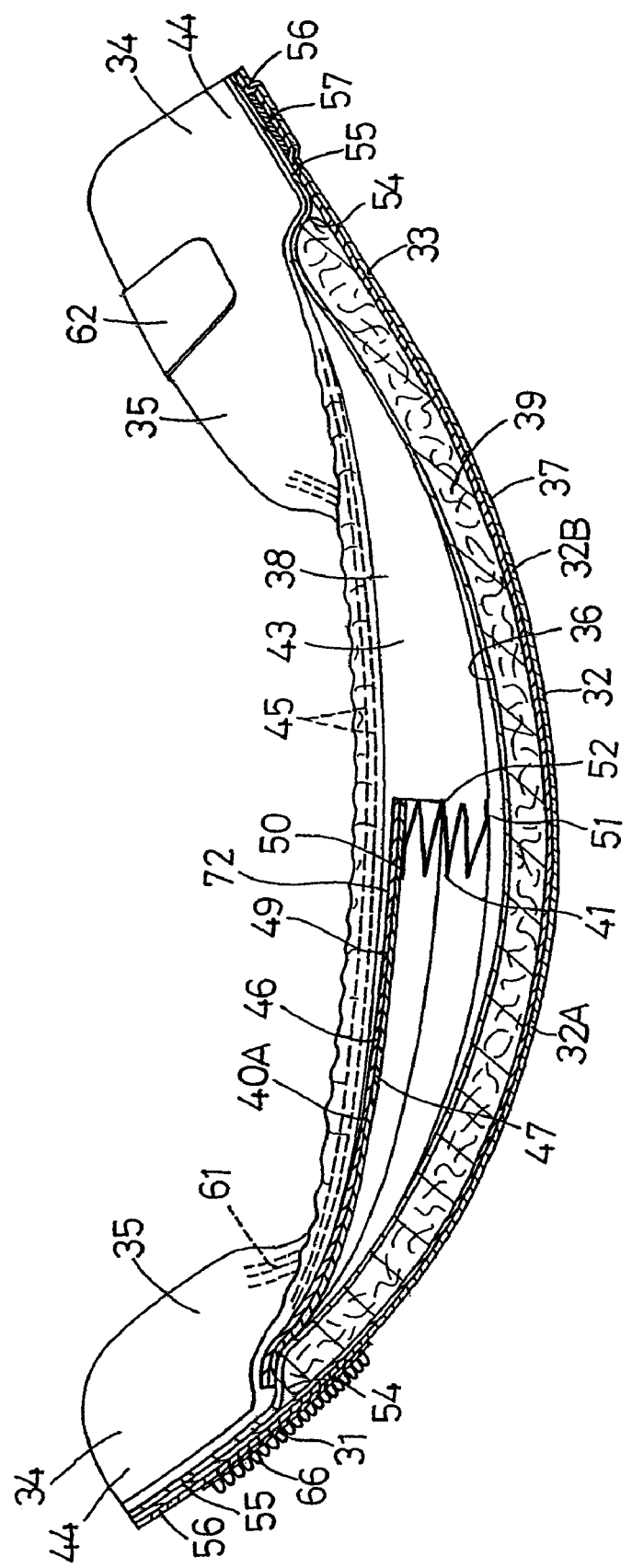
FIG. 19 is a sectional view taken along the line 19-19 in FIG. 18.
Figure 20:
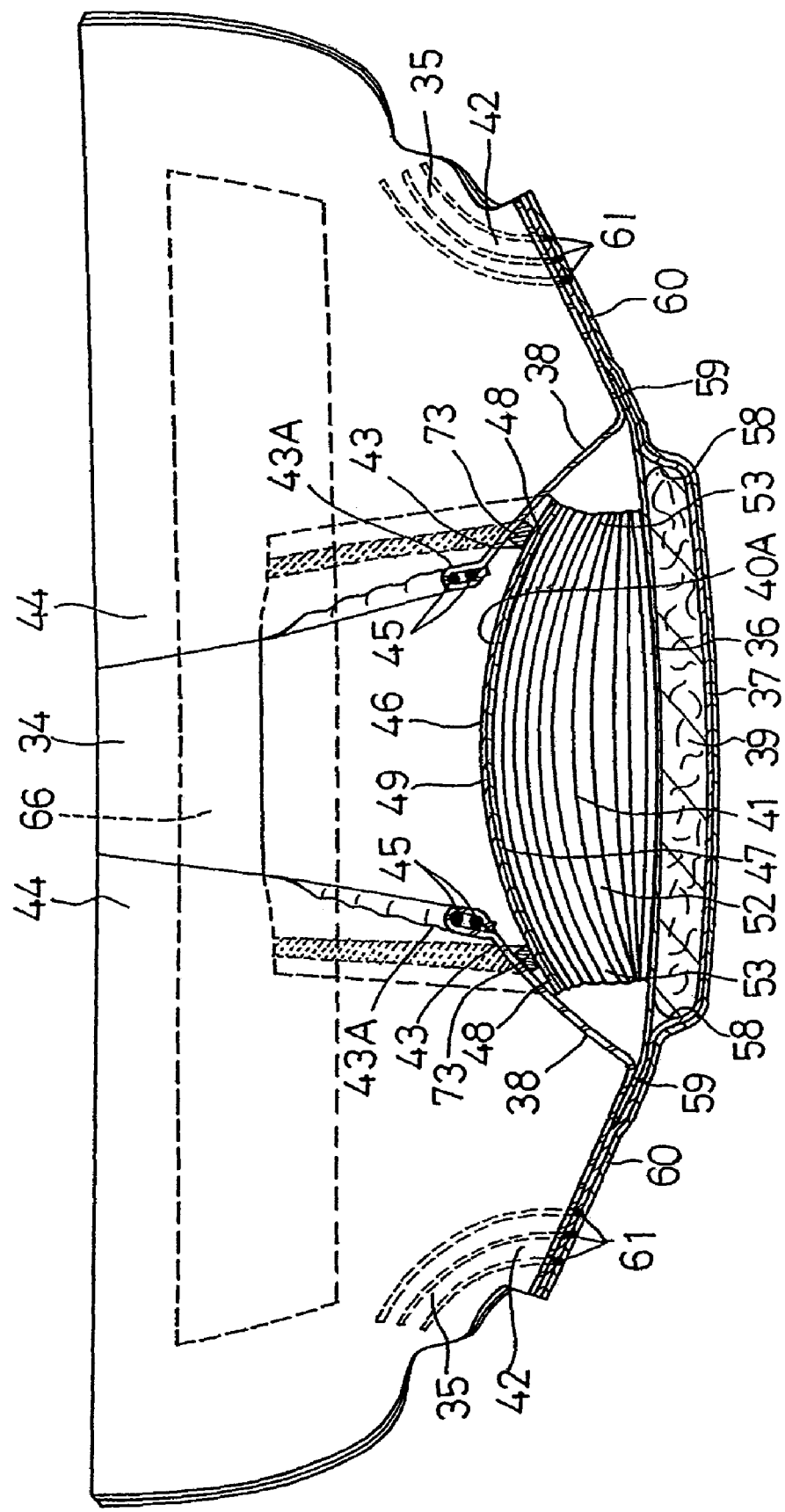
FIG. 20 is a sectional view taken along the line 20-20 in FIG. 18.

FIG. 18 is a perspective view showing a disposable wearing article 30E as further another preferred embodiment of the invention, FIG. 19 is a sectional view taken along the line 19-19 in FIG. 18 and FIG. 20 is a sectional view taken along the line 20-20 in FIG. 18. In FIG. 18, a transverse direction is indicated by an arrow L, a longitudinal direction is indicated by an arrow M and a thickness direction is indicated by an arrow N.

The article 30E is similar to the article 30A except that transversely opposite side edges 48 of the panel 40A are integrally bonded to the distal portions 43 of the respective leak-barrier cuffs 38, the panel 40A is laid in the front waist region 31 and the front half 32A of the crotch region 32 and the side edges 53 of the partition 41 are not integrally bonded to the article 30E. The components similar to those in the article 1A are denoted by the similar reference numerals and the description of the arrangement similar to that in the article 1A will be omitted here.

The panel 40A having a generally rectangular shape which is relatively long in the transverse direction is laid on the outer surface of the topsheet 36 in a rear half of the front waist region 31 and a front half area 32A of the crotch region 32 divided by a transverse center line L1. The panel 40A comprises a pair of hydrophilic nonwoven fabric layers 46, 47 (which is water-absorbent) placed upon each other. These nonwoven fabric layers 46, 47 have mutually opposed surfaces intermittently and permanently bonded to each other by means of adhesive (not shown). The panel 40A has transversely opposite side edges 48 integrally bonded to the distal portions 43 of the respective leak-barrier cuffs 38 and the intermediate region 49 defined between the side edges 48. The side edges 48 as well as the intermediate region 49 are spaced apart upward from the outer surface of the topsheet 36 as the distal portions 43 of the respective leak-barrier cuffs 38 rise up above the topsheet 36.

The partition 41 is interposed between the topsheet 36 and the panel 40A and laid in the vicinity of the transverse center line L1, i.e., the inner end portion 72 of the intermediate portion 49 of the panel 40A adjacent the transverse center line L1. The partition 41 has upper and lower edges 50, 51, a middle portion 52 and transversely opposite side edges 53 lying on the side portions 35 of the article 30E. The middle portion 52 and the side edges 53 are folded in three in the thickness direction of the article 30E. The side edges 53 are left free from the topsheet 36 as well as from the panel 40A.

Figure 21:
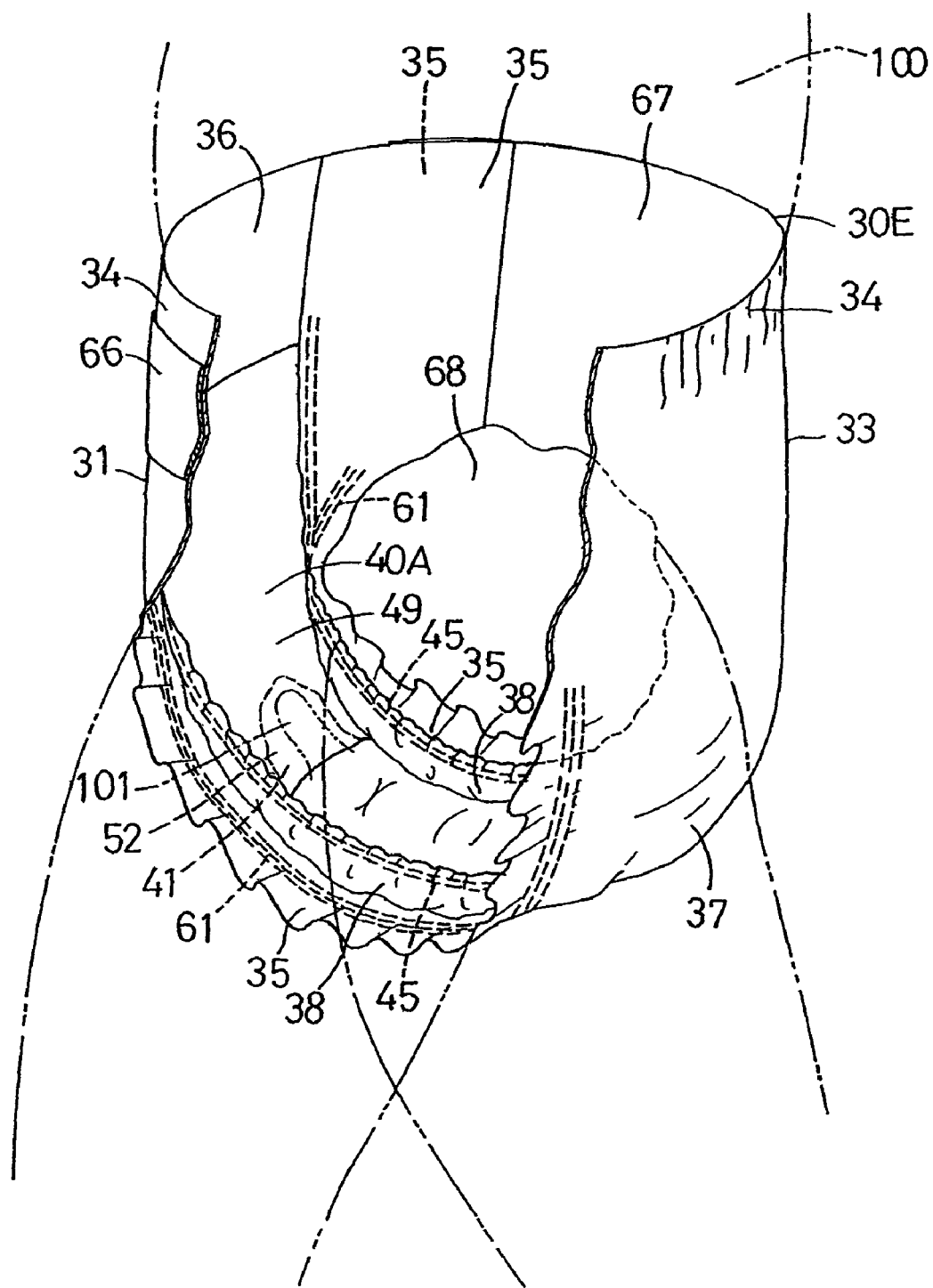
FIG. 21 is a perspective view showing the article of FIG. 18 as put on the wearer's body.

FIG. 21 is a perspective view showing the article 30E of FIG. 18 as put on the wearer's body, in which the front and rear waist regions 31, 33 are illustrated as partially cut away on one side of the waist. Sequential procedures to put the article 30E on the wearer's body are the same as in the case of the article 30A and the description thereof will be omitted here. After the article 30E has been put on the wearer's body, the buttock of the wearer 100 is in contact with the outer surface of the topsheet 36 and the penis 101 of the wearer 100 is in contact with the outer surface of the intermediate region 49 of the panel 40E. The intermediate region 49 of the panel 40A is spaced apart upward from the outer surface of the topsheet 36 as the distal portions 43 of the respective leak-barrier cuffs 38 rise up above the topsheet 36.

In the article 30E, through the side edges 53 of the partition 41 are not bonded to the distal portions 43 of the cuffs 38, the middle portion 52 of the partition 41 forms the pocket-like barrier adapted to prevent loose passage discharged onto the rear half 32B of the crotch region 32 and onto the rear waist region 33 from further flowing into the front half 32A of the crotch region 32 and into the front waist region 31 even when such loose passage spreads on the outer surface of the topsheet 36. Even if a large amount of loose passage is discharged on the article 30E, such a large amount of loose passage is reliably received by the pocket-like barrier formed by the partition 41 and there is no anxiety that such loose passage might flow beyond the partition 41 to the outer surface of the panel 40A.

Stock materials for the topsheet 36 is not limited to the hydrophilic fibrous nonwoven fabric but may be also selected from the group consisting of a hydrophobic fibrous nonwoven fabric having a plurality of perforations and a plastic film having a plurality of fine apertures. Stock materials for the backsheet 37 is not limited to the composite nonwoven fabric but may be selected from the group consisting of a hydrophobic fibrous nonwoven fabric, a breathable liquid-impervious plastic film and a composite sheet comprising a hydrophobic fibrous nonwoven fabric and a breathable plastic film laminated on each other. Stock materials for the partition 41 is not limited to a plastic film but it is also possible to use a hydrophobic fibrous nonwoven fabric to form this partition 41. It is possible without departing from the scope of the invention to form the backsheet 37, the leak-barrier cuffs 38 and the partition 41 using a composite nonwoven fabric (SM nonwoven fabric, SMS nonwoven fabric or SMMS nonwoven fabric) consisting of a melt blown fibrous nonwoven fabric having a high water-resistance and a spunbond fibrous nonwoven fabric being high in strength as well as in flexibility laminated on at least one side of the melt blown fibrous nonwoven fabric.

Stock materials for the fibrous nonwoven fabric layers may be selected from the group consisting of spun lace-, needle punch-, melt blown-, thermal bond-, spunbond- and chemical bond-nonwoven fabric layers. Component fibers of these nonwoven fabric layers may be selected from the group consisting of polyester-, polyacrylonitril-, polyvinyl chloride-, polyethylene-, polypropylene- and polystyrene-based fibers. It is also possible without departing from the scope of the invention to use the component fiber selected from the group consisting of core-sheath conjugate fibers, side-by-side conjugate fibers, modified macaroni fiber, microporous fibers and fused type conjugate fibers.

Integrally bonding of the elements 36, 37 to each other, integrally bonding of the elements 36, 37 to the leak-barrier cuffs 38, bonding of the core 61 to the elements 36, 37, integrally bonding of the panel 40A, 40B, 40C, 40D to the elements 36, 37, 38 and integrally bonding of the elastic members 45, 57, 61 to the elements 36, 37, 36 may be achieved by using adhesive or welding technique such as heat-sealing or sonic sealing. Adhesive may be selected from the group consisting of hot melt adhesive, acrylic adhesive and rubber-based adhesive.

The adhesive is coated on the topsheet 36, the backsheet 37 and the leak-barrier cuffs 38 preferably in any one of spiral, wavy, zigzag, dotted or striped pattern. These elements 36, 37, 38 may be coated with adhesive in such patterns to define adhesive-coated regions and adhesive-free regions in these elements 36, 37, 38 and thereby to ensure that these elements 36, 37, 38 are intermittently and integrally bonded one to another, the core 39 is intermittently and integrally bonded to the elements 36, 37 and the elastic members 45, 57, 61 are intermittently and permanently bonded to the elements 36, 37, 38.

In the articles 30A, 30E, respectively, the panel 40A may be replaced by any one of the panels 40B, 40C and 40D. In the article 30B, the panel 40B may be replaced by any one of the panels 40A, 40C and 40D, respectively. In the article 30C, the panel 40C may be replaced by any one of the panels 40A, 40B and 40D, respectively. In the article 30D, the panel 40D may be replaced by any one of the panels 40A, 40B and 40C. In the articles 30A, 30B, 30C and 30D, it is also possible to lay the panels 40A, 40B, 40C and 40D, respectively, in the front half 32A of the crotch region 32 and in the front waist region 31. In the article 30E, it is also possible to lay the panel 40A in the front half 32A of the crotch region 32 alone. In the articles 30A and 30C, it is also possible to leave the transversely opposite side edges 35 free from the leak-barrier cuffs 38.

What is claimed is:

1. A disposable wearing article, comprising:
   a front waist region, a rear waist region, a crotch region extending between said two waist regions in a longitudinal direction of the article,
   longitudinally opposite end portions extending across said waist regions in a transverse direction of the article, and transversely opposite side portions extending between said front and rear waist regions in the longitudinal direction,
   a liquid-pervious topsheet adapted to face a wearer's skin in use, a liquid-impervious backsheet adapted to face away from the wearer's skin in use,
   a pair of leak-barrier cuffs laid on said topsheet and extending between said front and rear waist regions, and
   a liquid-absorbent core interposed between said topsheet and backsheets, and extending between said front and rear waist regions,
   wherein said leak-barrier cuffs have
      proximal portions bonded to said opposite side portions of the article so as to extend in the longitudinal direction,
      distal portions extending in the longitudinal direction and normally biased to rise up above said topsheet, and
      longitudinally opposite end portions collapsed in the transverse direction and bonded to said longitudinally opposite end portions of the article in such a collapsed state,
   said article further comprising:
   stretchable elastic members extending in the longitudinal direction and contractibly bonded to said distal portions of said leak-barrier cuffs,
   a skin-contactable panel extending between said leak-barrier cuffs in the transverse direction and being laid on said topsheet in at least a front half of said crotch region, wherein said crotch region is divided by a transverse center line bisecting a longitudinal dimension of said article into said front half and a rear half, and
   a partition interposed between said topsheet and said panel, and extending between said leak-barrier cuffs in the transverse direction in a vicinity of said transverse center line,
   wherein
   said panel has transversely opposite side edges bonded to the distal potions of said leak-barrier cuffs, respectively, and an intermediate region defined between said side edges,
   said partition has an upper edge bonded to said panel, a lower edge bonded to said topsheet, and a middle portion between said upper and lower edges, said middle portion being folded at least into two in a thickness direction of said article to form a barrier against bodily wastes between said topsheet and said panel,
   wherein said panel is formed from at least one water-absorbent sheet.

2. The wearing article defined by claim 1,
   wherein said panel further comprises an absorbent core material wrapped with said water-absorbent sheet, and
   wherein said absorbent core material is at least one of a fibrous absorbent core and a foam material containing therein a plurality of cells.

3. The wearing article defined by claim 1, wherein
   said water-absorbent sheet is adapted to face the wearer's skin in use, and
   said panel is further formed from
      a liquid-impervious sheet adapted to face away from the wearer's skin in use, and
      an absorbent core material interposed between said water-absorbent sheet and said liquid-impervious sheet, and
   said absorbent core material is at least one of a fibrous absorbent core and a foam material containing therein a plurality of cells.

4. The wearing article defined by claim 1, wherein
   said panel and said partition are laid between said leak-barrier cuffs,
   the intermediate region of said panel is bonded directly to the distal portions of said leak-barrier cuffs, respectively, and said intermediate region of said panel is spaced upward from said topsheet as said distal portions of said leak-barrier cuffs rise up under contraction of said elastic members so that the middle portion of said partition extends upwardly in the thickness direction of the article between said topsheet and said panel to define said barrier.

5. The wearing article defined by claim 1, further comprising an elastically stretchable spacer extending in the transverse direction and being interposed in a stretched state between said topsheet and said panel,
 wherein said spacer has
  transversely opposite ends bonded to the side edges of said panel, respectively, and
  an intermediate portion defined between said transversely opposite side edges,
 wherein, under a contractile force of said spacer, the transversely opposite ends are drawn toward each other in the transverse direction of said article while the intermediate region of said panel is spaced upward from said topsheet to define an upward convex arc so that the middle portion of said partition extends upwardly in the thickness direction of the article between said topsheet and said panel to define said barrier,
 wherein said partition is entirely located in the front half of said crotch region; and
 wherein said spacer is entirely located forward of said partition in the longitudinal direction.

6. The wearing article defined by claim 5, wherein said spacer is completely located below said panel and has a maximum dimension measured in the longitudinal direction of the article smaller than that of said panel.

7. The wearing article defined by claim 5, wherein the intermediate portion of the spacer is free of direct attachment to said panel and said topsheet and is located between and spaced from said panel and topsheet when the spacer contracts.

8. The wearing article defined by claim 5, wherein the transversely opposite ends of said spacer are disposed between and bonded to the transversely opposite side portions of said article and the proximal portions of the leak-barrier cuffs, respectively.

9. The wearing article defined by claim 1, wherein
 said middle portion of the partition is repeatedly folded multiple times in the thickness direction of said article to define a bellows structure, and
 the middle portion that defines said bellows structure is entirely free of direct attachment to both the panel and the topsheet.

10. The wearing article defined by claim 9, wherein said bellows structure is completely located between the panel and the topsheet as seen in the thickness direction.

11. The wearing article defined by claim 10, wherein said bellows structure comprises 4 or more folds.

* * * * *